US012637399B2

(12) United States Patent (10) Patent No.: US 12,637,399 B2
Snell et al. (45) **Date of Patent: \*May 26, 2026**

(54) FLEXIBLE PRODUCTION OF BENZENE AND DERIVATIVES THEREOF VIA OLIGOMERIZATION OF ETHYLENE

(71) Applicant: Chevron Phillips Chemical Company LP, The Woodlands, TX (US)

(72) Inventors: Ryan W. Snell, Jubail Industrial City (SA); Xianghong Hao, Kingwood, TX (US); Brook L. Small, Kingwood, TX (US); Bruce E. Kreischer, Kingwood, TX (US); Scott G. Morrison, Kingwood, TX (US); Gregory G. Hendrickson, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 16 days.

This patent is subject to a terminal disclaimer.

(21) Appl. No.: 18/347,055

(22) Filed: Jul. 5, 2023

(65) Prior Publication Data

US 2024/0010584 A1 Jan. 11, 2024

Related U.S. Application Data

(60) Provisional application No. 63/367,651, filed on Jul. 5, 2022.

(51) Int. Cl.
| | |
|---|---|
| *C07C 2/08* | (2006.01) |
| *C07C 5/03* | (2006.01) |
| *C07C 5/393* | (2006.01) |
| *C07C 15/04* | (2006.01) |

(52) U.S. Cl.
CPC ............... *C07C 15/04* (2013.01); *C07C 2/08* (2013.01); *C07C 5/03* (2013.01); *C07C 5/393* (2013.01)

(58) Field of Classification Search
CPC .. C07C 15/04; C07C 2/08; C07C 2/66; C07C 4/04; C07C 5/03; C07C 5/10; C07C 5/327; C07C 5/333; C07C 5/41; C10G 57/02
See application file for complete search history.

(56) References Cited

U.S. PATENT DOCUMENTS

| | | | |
|---|---|---|---|
| 3,274,978 A | 9/1966 | Palchik |
| 3,392,211 A | 7/1968 | Buschmann |
| 3,403,722 A | 10/1968 | Woebcke |

(Continued)

FOREIGN PATENT DOCUMENTS

| | | |
|---|---|---|
| WO | 2010051415 A1 | 5/2010 |
| WO | 2015094207 A1 | 6/2015 |
| WO | 2015095347 A1 | 6/2015 |

OTHER PUBLICATIONS

International Search Report and Written Opinion issued in corresponding PCT Application No. PCT/US2023/082765, mailed on Jul. 1, 2024, 9 pp.

(Continued)

*Primary Examiner* — In Suk C Bullock
*Assistant Examiner* — Jason Y Chong
(74) *Attorney, Agent, or Firm* — Scheef & Stone, L.L.P.; Keith C. Rawlins, Esq.

(57) ABSTRACT

Disclosed is oligomerization of ethylene to form 1-hexene in combination with aromatization of the 1-hexene formed by oligomerization, to form benzene.

19 Claims, 12 Drawing Sheets

(56) References Cited

U.S. PATENT DOCUMENTS

| | | | |
|---|---|---|---|
| 3,407,789 A | 10/1968 | Hallee | |
| 3,679,762 A | 7/1972 | La Hue | |
| 3,820,955 A | 6/1974 | Woebcke | |
| 3,827,968 A * | 8/1974 | Givens | C10L 1/06 |
| | | | 585/304 |
| 4,128,595 A | 12/1978 | Montgomery | |
| 4,151,071 A * | 4/1979 | Myers | B01J 23/26 |
| | | | 585/407 |
| 4,347,392 A | 8/1982 | Cosyns | |
| 4,351,275 A | 9/1982 | Bhojwani | |
| 4,499,055 A | 2/1985 | Dinicolantonio | |
| 4,571,442 A | 2/1986 | Cosyns | |
| 4,762,956 A | 8/1988 | Liu | |
| 4,780,196 A | 10/1988 | Alagy | |
| 5,059,732 A | 10/1991 | Cosyns | |
| 5,151,158 A | 9/1992 | Bowen | |
| 5,401,386 A | 3/1995 | Morrison | |
| 5,427,655 A | 6/1995 | Woebcke | |
| 5,488,024 A | 1/1996 | Cheung | |
| 5,489,565 A | 2/1996 | Cheung | |
| 5,510,550 A | 4/1996 | Cheung | |
| 5,543,375 A | 8/1996 | Lashier | |
| 5,563,312 A | 10/1996 | Knudsen | |
| 5,583,274 A | 12/1996 | Cheung | |
| 5,585,318 A | 12/1996 | Johnson | |
| 5,587,348 A | 12/1996 | Brown | |
| 5,602,290 A | 2/1997 | Fallon | |
| 5,689,028 A | 11/1997 | Lashier | |
| 5,698,752 A | 12/1997 | Brown | |
| 5,856,607 A * | 1/1999 | Kim | C07C 15/073 |
| | | | 585/314 |
| 5,877,367 A | 3/1999 | Witte | |
| 5,880,320 A | 3/1999 | Netzer | |
| 6,004,452 A | 12/1999 | Ash | |
| 6,111,156 A * | 8/2000 | Oballa | C10G 69/06 |
| | | | 585/329 |
| 6,127,310 A | 10/2000 | Brown | |
| 6,190,539 B1 | 2/2001 | Holtermann | |
| 6,252,126 B1 | 6/2001 | Netzer | |
| 6,790,342 B1 | 9/2004 | Porter | |
| 6,812,180 B2 | 11/2004 | Fukunaga | |
| 7,153,801 B2 | 12/2006 | Wu | |
| 7,157,612 B2 | 1/2007 | Ewert | |
| 7,300,904 B2 | 11/2007 | Dixon | |
| 7,361,623 B2 | 4/2008 | Dixon | |
| 7,554,001 B2 | 6/2009 | Dixon | |
| 7,718,838 B2 | 5/2010 | Woodard | |
| 7,932,425 B2 | 4/2011 | Blessing | |
| 7,994,363 B2 | 8/2011 | Gao | |
| 8,252,956 B2 | 8/2012 | Gao | |
| 8,680,003 B2 | 3/2014 | Sydora | |
| 8,865,610 B2 | 10/2014 | Sydora | |
| 9,199,893 B2 * | 12/2015 | Lapinski | C07C 2/76 |
| 10,435,336 B2 | 10/2019 | Kreischer | |
| 2010/0274065 A1 | 10/2010 | Sydora | |
| 2011/0263917 A1 | 10/2011 | Van Hal | |
| 2014/0058144 A1 | 2/2014 | Bricker | |
| 2021/0138429 A1 | 5/2021 | Yao | |

OTHER PUBLICATIONS

Agapie, et al., "Mechanistic Studies of Olefin and Alkyne Trimerization with Chromium Catalysts: Deuterium Labeling and Studies of Regiochemistry Using a Model Chromacyclopentane Complex." J. Am. Chem. Soc., 2007, 129, 14281-14295.

Agapie, T., "Selective Ethylene Oligomerization: Recent advances in chromium catalysis and mechanistic Investigations," Coordination Chemistry Reviews, 2011, vol. 255, pp. 861-880, Elsevier B.V.

Bollmann, et al., "Ethylene Tetramerization: A New Route to Produce 1-Octene in Exceptionally High Selectives." J. Am. Chem. Soc., 2004, 126, 14712-14713.

Carter, et. al., "High Activity Ethylene Trimerisation Catalysts Based on Diphosphine Ligands." Chem. Commun., 2002, 858-859.

Chang, New Projects May Raise US Ethylene Capacity by 52%, PE by 47%, ICIS, Jan. 14, 2014.

Hui, Outlook '14: Asia Methanol Demand to Strengthen on New Uses, ICIS, Dec. 24, 2012.

Kearney, Apr. 30, 2014 https://www.kearney.com/industry/chemicals/article/-/insights/shale-gas-threat-or-opportunity-for-the-gcc-article#:~:text=The%20U.S.%20shale%20gas%20revolution,liquid%20cracking%20and%20its%20derivatives.

Nash, Aromatization over Platinum/Zeolite L Catalysts: The Effect of Oxygenates, Thesis submitted in fulfillment for the degree of Doctor of Philosophy, University of Cape Town, Feb. 1997.

Piet W.N.M. van Leeuwen, et al., "New Processes for the Selective Production of 1-Octene," Coordination Chemistry Reviews, 255, 2011, pp. 1499-1517.

Sydora, et al. "Selective Ethylene Tri-/Tetramerization Catalysts." ACS Catalysis. Feb. 2012. 2452.

* cited by examiner

FLEXIBLE PRODUCTION OF BENZENE AND DERIVATIVES THEREOF VIA OLIGOMERIZATION OF ETHYLENE

CROSS-REFERENCE TO RELATED APPLICATION

This application is a non-provisional patent application claiming the benefit of, and priority to, U.S. Provisional Patent Application No. 63/367,651, filed Jul. 5, 2022, which is incorporated by reference herein in its entirety.

TECHNICAL FIELD

The present disclosure relates to the integration of systems and processes associated with steam cracking, oligomerization reactions, and aromatization reactions such that benzene can be produced via oligomerization of ethylene.

BACKGROUND

Benzene, also known as benzol, mineral naphtha, phenyl hydride, and annulene, is an aromatic compound that is an important item of commerce. Benzene is found in crude oil, is a component of gasoline, and is a widely used industrial chemical including application in the manufacture of plastics, resins, synthetic fibers, rubber lubricants, dyes, detergents, drugs, pesticides, glues, adhesives, cleaning products, and paint strippers. Conventional methods of benzene production that begin with materials contained in crude oil are increasingly expensive due to increasing demand for crude oil. Methods of producing benzene using natural gas as a starting material can provide a lower cost alternative. Thus, additional novel and improved systems and methods for benzene production are desirable.

SUMMARY

Disclosed is a method comprising: contacting, in an oligomerization reactor, ethylene and an oligomerization catalyst to yield an oligomerization reactor effluent comprising 1-hexene; recovering 1-hexene from the oligomerization reactor effluent; and contacting, in an aromatization reactor, the 1-hexene recovered from the oligomerization reactor effluent with an aromatization catalyst to yield an aromatization reactor effluent comprising benzene.

A system comprising: an oligomerization reactor configured to contact ethylene with an oligomerization catalyst to yield an oligomerization reactor effluent comprising 1-hexene; and an aromatization reactor configured to contact 1-hexene recovered from the oligomerization reactor effluent with an aromatization catalyst to yield an aromatization reactor effluent comprising benzene.

DETAILED DESCRIPTION

I. Overview

Figure 1:
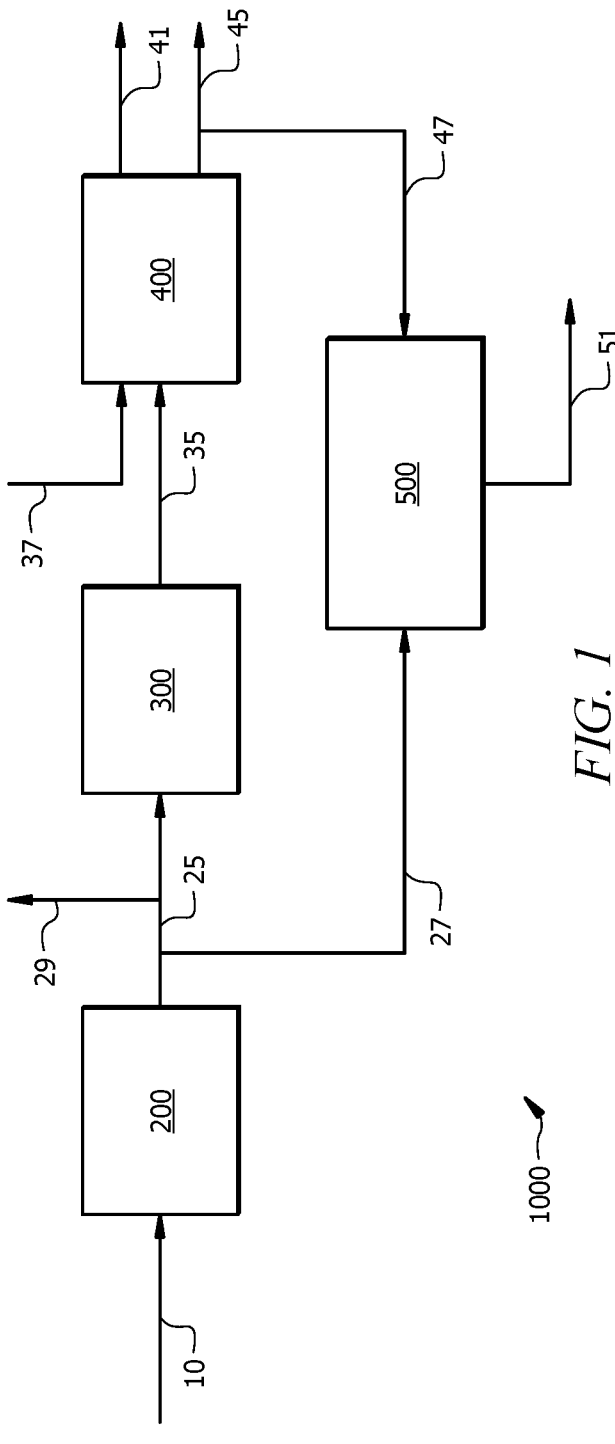
FIG. 1 illustrates a schematic of an integrated converting system.

It should be understood at the outset that although an illustrative implementation of one or more aspects are provided below, the disclosed systems, processes, and/or methods can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

Disclosed herein are systems, processes, apparatuses and methods for multi-step chemical converting wherein several chemical transformations are integrated into a single, continuous-flow system. The integrated converting systems as well as the processes, apparatuses, and methods associated therewith, are generally related to continuous-flow systems which integrate converting $C_{4-}$ hydrocarbons, such as hydrocarbons derived from natural gas (e.g., ethane), into oligomer intermediates (e.g., 1-hexene), which are further converted into arenes (e.g., benzene).

As disclosed herein, a method of utilizing an integrated converting system generally comprises the steps of (a) cracking a hydrocarbon feedstock (e.g., natural gas) in a cracking process (e.g., steam cracker) to yield a cracker effluent comprising a monomer (e.g., ethylene); (b) flowing the monomer recovered from the cracker effluent to an oligomerization process; (c) contacting, in the oligomerization process, the monomer and an oligomerization catalyst to yield an oligomerization reactor effluent comprising an oligomer (e.g., 1-hexene); (d) flowing the oligomer recovered from the oligomerization reactor effluent to an aromatization process; and (e) contacting, in the aromatization process, the oligomer with an aromatization catalyst to yield an aromatization effluent comprising an arene (e.g., benzene). In an aspect, the integrated converting systems of the present disclosure are continuous, serial-flow systems wherein the cracking process is connected to the oligomerization process which is connected to the aromatization process wherein the cracker effluent, or a stream derived therefrom, flows into the oligomerization process and the oligomerization reactor effluent produced therein, or a stream derived therefrom, flows into the aromatization process. In some aspects as described in more detail herein, an integrated converting system can include a hydrotreating process connected between the oligomerization process and the aromatization process.

Throughout the systems, processes, and methods disclosed herein numerous streams and products (e.g., ethylene, 1-hexene, benzene, ethylbenzene, styrene), are recovered from reactors and/or process streams. One having ordinary skill in the art will recognize that a stream or product may be recovered directly from a reactor or process in which it is formed; alternatively, the stream or product may be recovered (e.g., via a separation process) from another process and/or stream located downstream of where it was formed.

II. Definitions

The following definitions are provided in order to aid those skilled in the art in understanding the detailed description of the present disclosure. Unless otherwise defined herein, scientific and technical terms used in connection with the present disclosure shall have the meanings that are commonly understood by those of ordinary skill in the art to which this disclosure belongs. Further, unless otherwise required by context, singular terms shall include pluralities and plural terms shall include the singular.

Further, certain features of the present disclosure which are, for clarity, described herein in the context of separate aspects, may also be provided in combination in a single aspect. Conversely, various features of the disclosure that are, for brevity, described in the context of a single aspect, may also be provided separately or in any sub-combination.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the periodic table are indicated using the numbering scheme indicated in the version of the periodic table of elements published in *Chemical and Engineering News,* 63(5), 27, 1985. In some instances a group of elements may be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements.

General formulas $C_{A+}$ and $C_{A-}$ represent the number of carbon atoms in the molecular formula of an organic molecule (e.g., a hydrocarbon) where A is a whole number. For example, $C_{3+}$ represents compounds with three or more carbon atoms per molecule and $C_{5-}$ represents compounds with five or less carbon atoms per molecule Unless explicitly stated otherwise in defined circumstances, all percentages, parts, ratios, and like amounts used herein are defined by weight.

The term "olefin" whenever used in this specification and claims refers to compounds that have at least one carbon-carbon double bond that is not part of an aromatic ring or ring system. The term "olefin" includes aliphatic and aromatic, cyclic and cyclic, and/or linear and branched compounds having at least one carbon-carbon double bond that is not part of an aromatic ring or ring system unless specifically stated otherwise. The term "olefin," by itself, does not indicate the presence or absence of heteroatoms and/or the presence or absence of other carbon-carbon double bonds unless explicitly indicated. Olefins having only one, only two, only three, etc. carbon-carbon double bonds can be identified by use of the term "mono," "di," "tri," etc. within the name of the olefin. The olefins can be further identified by the position of the carbon-carbon double bond(s).

The term "reactor effluent," and it derivatives (e.g. oligomerization reactor effluent) generally refers to all the material which exits the reactor. The term "reactor effluent," and its derivatives, can also be prefaced with other descriptors that limit the portion of the reactor effluent being referenced. For example, while the term "reactor effluent" would refer to all material exiting the reactor (e.g. product and solvent or diluent, among others), the term "olefin reactor effluent" refers to the effluent of the reactor which contains an olefin (i.e. carbon-carbon) double bond.

The term "oligomerization," and its derivatives, refers to processes which produce a mixture of products containing at least 70 weight percent products containing from 2 to 30 monomer units. Similarly, an "oligomer" is a product that contains from 2 to 30 monomer units while an "oligomerization product" includes all product made by the "oligomerization" process including the "oligomers" and products which are not "oligomers" (e.g. product which contain more than 30 monomer units). It should be noted that the monomer units in the "oligomer" or "oligomerization product" do not have to be the same. For example, an "oligomer" or "oligomerization product" of an "oligomerization" process using ethylene and propylene as monomers can contain both ethylene and/or propylene units.

The term "trimerization," and it derivatives, refers to a process which produces a mixture of products containing at least 70 weight percent products containing three and only three monomer units. A "trimer" is a product which contains three and only three monomer units while a "trimerization product" includes all products made by the trimerization process including trimer and product which are not trimer (e.g. dimers or tetramers). Generally, an olefin trimerization reduces number of olefinic bonds, i.e., carbon-carbon double bonds, by two when considering the number of olefin bonds in the monomer units and the number of olefin bonds in the trimer. It should be noted that the monomer units in the "trimer" or "trimerization product" do not have be the same. For example, a "trimer" of a "trimerization" process using ethylene and butene as monomers can contain ethylene and/or butene monomer units. That is to say the "trimer" will include $C_6$, $C_8$, $C_{10}$, and $C_{12}$ products. In another example, a "trimer" of a "trimerization" process using ethylene as the monomer can contain ethylene monomer units. It should also be noted that a single molecule can contain two monomer units. For example, dienes such as 1,3-butadiene and 1,4-pentadiene have two monomer units within one molecule.

The term monomer refers to a $C_{4-}$ hydrocarbon having a molecular structure containing a single carbon-carbon double bond. For example, the monomer may be a $C_2$ monoolefin The term oligomer refers to a $C_{6+}$ hydrocarbon having a molecular structure containing at least one carbon-carbon double bond. For example, the oligomer may be a $C_6$ monoolefin.

The term arene refers to monocyclic $C_6$ to $C_{14}$ aromatic compounds.

Cetane number is a measure of the ignition properties of diesel fuel relative to cetane ($C_{16}H_{34}$), as a standard.

The smoke point of an oil or fat is the temperature at which, under specific and defined conditions, it begins to produce a continuous bluish smoke that becomes clearly visible.

A further understanding of the aspects of the present disclosure can be found by referring to the attached schematic flow diagrams, in combination with the following descriptions. Various additional pumps, valves, heaters, coolers and other conventional equipment necessary for the practice of the present disclosure herein will be familiar to one skilled in the art. In some instances, said additional equipment may have been omitted from the drawings for the sake of clarity. The descriptions of the drawings provide one method for operating the process. However, it is understood that while these drawings are general representations of the process, minor changes can be made in adapting the drawings to the various conditions within the scope of the disclosure. It is also understood that numerical references in the drawings are consistent throughout the drawings. For example, an inlet stream 10, comprising a hydrocarbon feedstock, is a hydrocarbon feedstock inlet stream in all drawings. Unless otherwise explicitly disclosed, the functions and components of a process (e.g., a process component or unit) in one integrated converting system are substantially the same within another integrated converting system comprising that process (e.g., the same process component or unit). In other words, the functions and components of cracking process 200 within integrated converting system 1000 are substantially the same as the functions and components of cracking process 200 within integrated converting system 1100, or the functions and components of cracking process 200 within integrated converting system 1200, etc., unless otherwise explicitly disclosed.

III. Integrated Converting System 1000

Referring to FIG. 1, an integrated converting system 1000 is described. Integrated converting system 1000 generally comprises cracking process 200, oligomerization process 300, aromatization process 400, and derivatization process 500.

In the integrated converting systems disclosed herein, various system components can be in fluid communication via one or more conduits (e.g., pipes, tubing, flow lines, etc.) suitable for the conveyance of a particular stream, for example as shown in detail by the numbered streams in FIG. 1.

A hydrocarbon feedstock 10 flows into cracking process 200 wherein hydrocarbons are converted (i.e., cracked), into monomers. In an aspect, the monomer comprises ethylene. Cracking process 200 may comprise any cracking process suitable for producing ethylene as disclosed herein. The cracking process 200 may be a steam cracker for converting one or more hydrocarbons into ethylene. Methods of converting hydrocarbons into ethylene are disclosed in U.S. Pat. No. 6,790,342 which is incorporated herein by reference in its entirety. Any method of producing ethylene disclosed in U.S. Pat. No. 6,790,342 may be utilized herein. The hydrocarbon feedstock 10 comprises any one or more hydrocarbons suitable for use as disclosed herein. For example, the hydrocarbons may comprise non-aromatic hydrocarbons, aromatic hydrocarbons, and a combination thereof. The hydrocarbons may be derived from natural gas, gas condensates, gas oils, or combinations thereof. In an aspect, the hydrocarbons comprise ethane, propane, butanes, pentanes, naphthas, or combinations thereof. In a further aspect, the hydrocarbon feedstock 10 comprises ethane wherein the ethane may be derived from a source of natural gas.

In a particular aspect, an amount of ethane in the hydrocarbon feedstock 10 is in a range of from about 10 wt. % to about 95 wt. %; alternatively, about 20 wt. % to about 80 wt. %, or alternatively, about 40 wt. % to about 60 wt. %, based upon a total weight of the hydrocarbon feedstock 10.

III.A. Cracking Process 200

Figure 2:
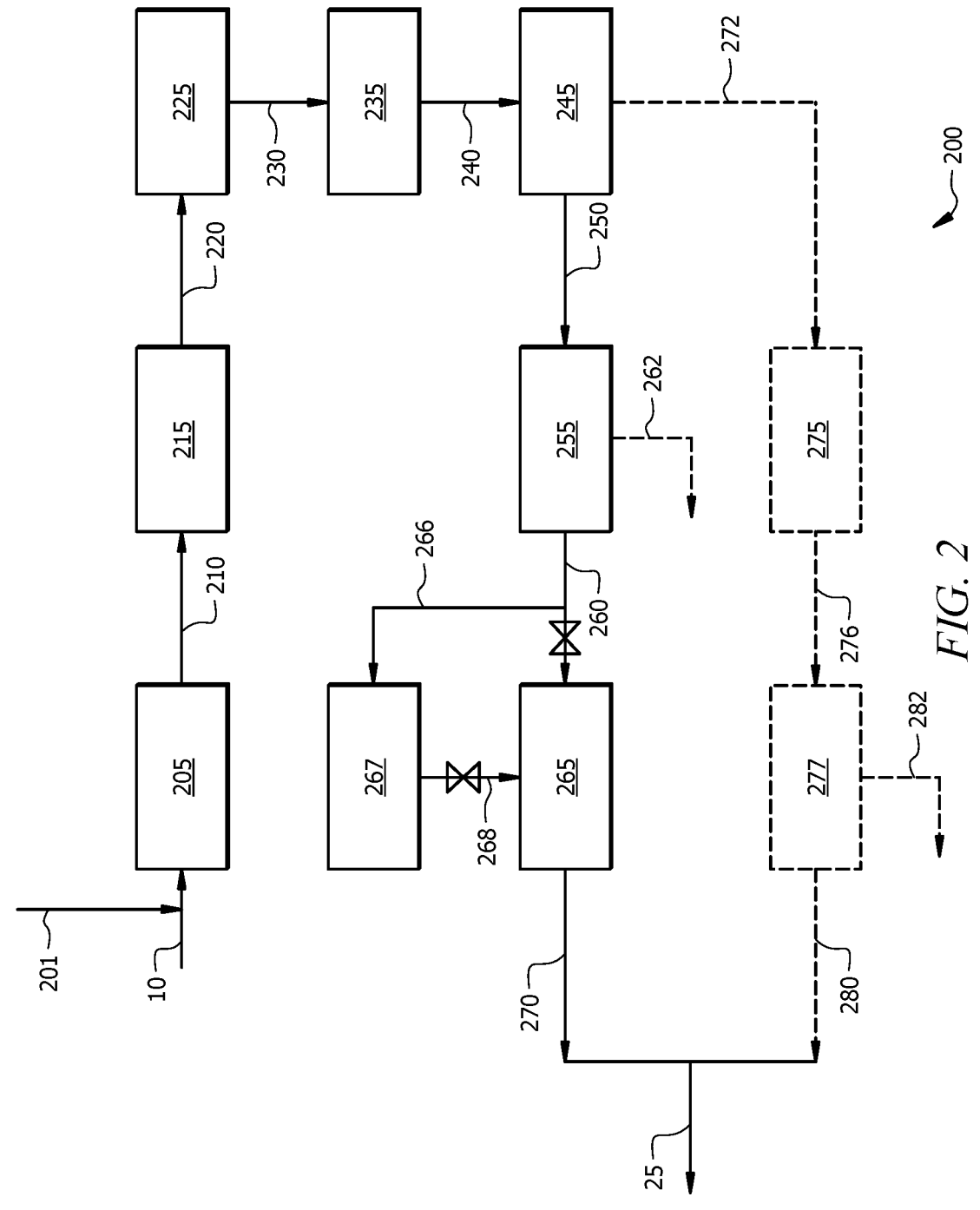
FIG. 2 illustrates a schematic of a cracking process.
Figure 9:
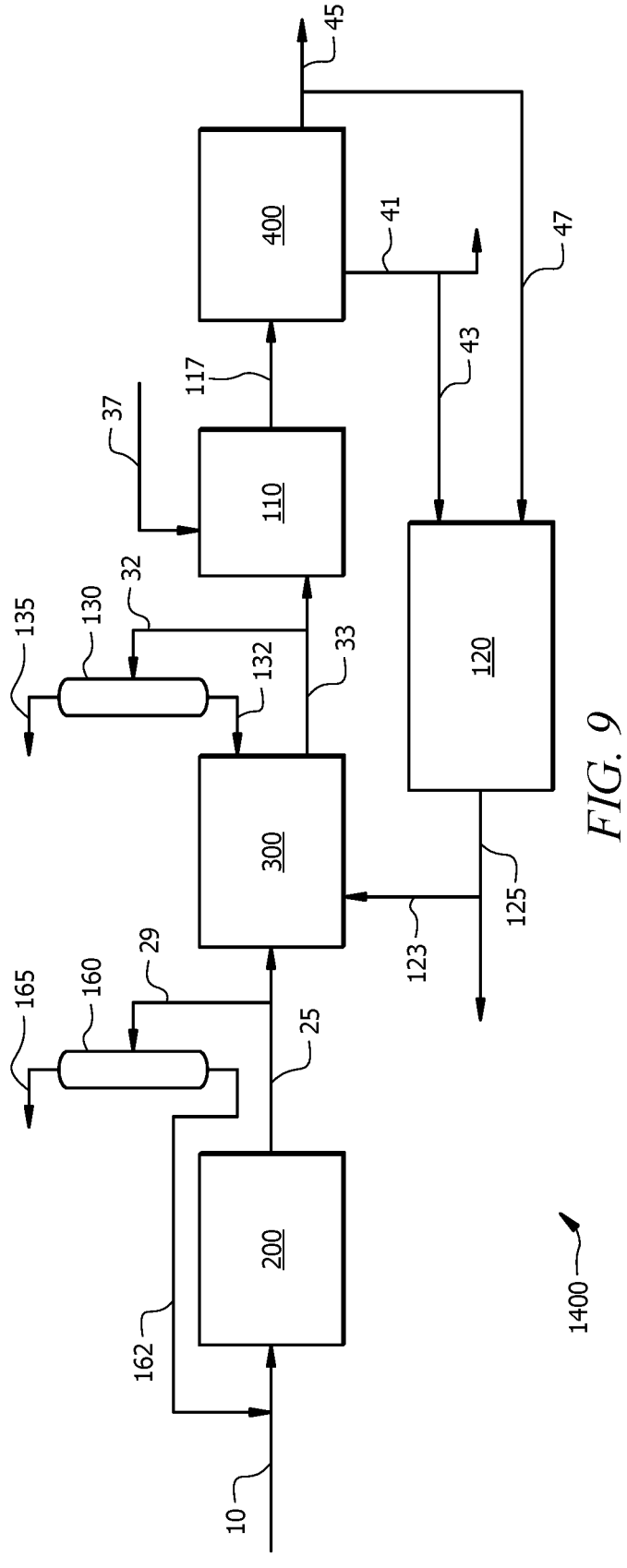
FIG. 9 illustrates a schematic of another integrated converting system.

Referring to FIG. 2, an aspect of cracking process 200 is described. The hydrocarbon feedstock 10 is optionally combined with a hydrocarbon recycle stream 201. The hydrocarbon recycle stream 201 may be comprised of other streams of an integrated reforming system disclosed herein. For example, the hydrocarbon recycle stream 201 may be comprised of one or more streams selected from the group consisting of a $C_{3+}$ stream 262 and/or an alternate $C_{3+}$ stream 282 of cracking process 200; a heavies effluent 336 and/or a by-product effluent 352 of FIG. 3; a $C_2$ effluent 488 of FIG. 4; a polyalkylated stream 527 and/or an aromatics stream 545 of FIG. 5; an ethane split stream 162 of FIG. 9; and combinations thereof, all of which are further described herein. It is contemplated that some aspects of cracking process 200 may operate without the hydrocarbon recycle stream 201.

III.A.1. Flowscheme (1/2)

III.A.1.a. Cracking Zone & Effluent

Referring to FIG. 2, the hydrocarbon feedstock 10 is diluted with steam and fed into cracking zone 205 comprising a steam cracker wherein heating to an elevated temperature in the absence of oxygen produces a cracker effluent 210. Cracking zone 205 comprises one or more radiant furnace reactors capable of producing the cracker effluent 210. The products present in the cracker effluent 210 may vary depending upon the composition of the feed, the hydrocarbon-to-steam ratio, and on the cracking temperature and furnace residence time. In an aspect, cracking zone 205 may have a temperature in a range of from about 600° C. to about 1500° C.; alternatively, about 750° C. to about 900° C. In a further aspect, cracking zone 205 may have an inlet pressure in a range of from about 5 psig to about 400 psig (about 0.03 MPag to about 2.76 MPag); or alternatively, about 29 psig to about 45 psig (about 0.19 MPag to about 0.31 MPag); and an outlet pressure in a range of from about 0.5 psig to about 40 psig (about 0.0034 MPag to about 0.28 MPag); or alternatively, about 3.5 psig to about 11 psig (about 0.024 MPag to about 0.076 MPag). Radiant furnace reactors are disclosed in U.S. Pat. Nos. 5,151,158; 4,780, 196; 4,499,055; 3,274,978; 3,407,789; and 3,820,955, each of which is incorporated herein by reference in its entirety. In an aspect, the cracker effluent 210 comprises one or more monomers, hydrogen, methane, acetylene, ethane, $C_{3+}$ saturated hydrocarbons, steam, and combinations thereof. In a further aspect, the monomer(s) comprises ethylene, propylene, butene, or combinations thereof; or alternatively, ethylene.

An amount of ethylene in the cracker effluent 210 may be in a range of from about 10 wt. % to about 95 wt. %; alternatively, about 20 wt. % to about 80 wt. %; or alternatively, about 40 wt. % to about 70 wt. %, based upon a total weight of the cracker effluent 210. In a further aspect, the cracker effluent 210 may comprise from about 1 wt. % to about 20 wt. % hydrogen, from about 1 wt. % to about 30 wt. % methane, from about 1 wt. % to about 30 wt. % acetylene, from about 3 wt. % to about 45 wt. % ethane, from about 0 wt. % to about 25 wt. % $C_3$ hydrocarbons, and from about _____ wt. % to about _____ wt. % steam.

III.A.2. Flowscheme (2/2)

The cracker effluent 210 flows into quenching zone 215 to produce a quenched gas stream 220. In an aspect, an operating temperature of quenching zone 215 may be less than necessary to sustain a cracking reaction occurring within the cracker effluent 210. In an aspect, the cracker effluent 210 is cooled to a temperature below about 595° C.; alternatively, to a temperature in a range of about 30° C. to about 110° C. to form the quenched gas stream 220. Quenching can be effected by any means suitable to one having ordinary skill in the art. For example, the cracker effluent 210 may be passed to a quench boiler and quench tower where dilution steam can be removed and recycled back to the cracking furnaces. Methods for cooling the cracker effluent 210 are disclosed in U.S. Pat. Nos. 3,407,798; 5,427,655; 3,392,211; 4,351,275; and 3,403,722, each of which is incorporated herein by reference in its entirety. The quenched gas stream 220 flows into first compression zone 225 to produce a pressurized gas stream 230. In an aspect, the pressurized gas stream 230 may comprise a pressure in a range of from about 150 psig to about 650 psig (about 1.034 MPag to about 4.48 MPag). First compression zone 225 comprises one or more gas compressors wherein the gas compressors may be any gas compressor suitable for use as disclosed herein.

The pressurized gas stream 230 flows into de-acidifying zone 235 wherein hydrogen sulfide ($H_2S$) and carbon dioxide ($CO_2$) are removed to produce a wet gas stream 240. In an aspect, de-acidifying zone 235 removes a portion of the $H_2S$ and $CO_2$ within the pressurized gas stream 230. In a further aspect the wet gas stream 240 may have a $H_2S$ concentration of less than about 0.1 ppm by weight; alternatively, in a range of about 25 ppb to about 100 ppb by weight. In yet a further aspect, the wet gas stream 240 may have a $CO_2$ concentration of less than about 5 ppm by weight. Removal of $H_2S$ and $CO_2$ may be effected by any suitable means as determined by one having ordinary skill in the art and with the aid of this disclosure. In yet a further aspect, diethanolamine or caustic contactors may be used to remove at least a portion of the $H_2S$ and $CO_2$ comprising the pressurized gas stream 230. The wet gas stream 240 flows into drying zone 245 to produce a cracked gas stream 250. In an aspect, the water content of the cracked gas stream 250 is less than an amount needed to effect downstream operational problems. In a further aspect, the water content of the cracked gas stream 250 is less than about 10 ppm by weight. Drying in drying zone 245 may be effected by any suitable means as determined by one having ordinary skill in the art and with the aid of this disclosure. In an aspect, molecular sieve beds can be utilized to remove water from the wet gas stream 240.

The cracked gas stream 250 flows into deethanizer zone 255 to produce a $C_{2-}$ stream 260 and a $C_{3+}$ stream 262. Deethanizer zone 255 comprises a fractionator capable of producing the $C_{2-}$ stream 260 and the $C_{3+}$ stream 262. The $C_{2-}$ stream 260 may comprise hydrogen, methane, ethane, acetylene, ethylene or combinations thereof. The $C_{3+}$ stream 262 comprises $C_3$ hydrocarbons and heavier constituents and, in an aspect, may be combined with the hydrocarbon recycle stream 201. The $C_{2-}$ stream 260 flows into hydrogenation zone 265 wherein a portion of the acetylene within the $C_{2-}$ stream 260 may be removed. An ethylene stream 270 is recovered from hydrogenation zone 265. Hydrogenation of the $C_{2-}$ stream 260 may be performed by any means suitable as determined by one having ordinary skill in the art and with the aid of this disclosure. For example, an acetylene reactor containing a selective hydrogenation catalyst can be utilized to hydrogenate a portion of the acetylene within the $C_{2-}$ stream 260 selectively to ethylene (in preference to hydrogenation to acetylene to ethane). Typically, Group VIII metal hydrogenation catalysts are utilized. Selective hydrogenation catalysts are disclosed in U.S. Pat. Nos. 3,679,762; 4,571,442; 4,347,392; 4,128,595; 5,059,732; 5,488,024; 5,489,565; 5,520,550; 5,583,274; 5,698,752; 5,585,318; 5,587,348; 6,127,310 and 4,762,956, each of which is incorporated herein by reference in its entirety. Operating conditions in hydrogenation zone 265 may be any combination of conditions suitable as determined by one having ordinary skill in the art and with the aid of this disclosure. In an aspect, the temperature and pressure in hydrogenation zone 265 may be at levels capable to hydrogenate a portion of the acetylene in the $C_{2-}$ stream 260 to ethylene. In a further aspect, hydrogenation zone 265 may have a temperature in a range of from about 10° C. to about 205° C. In yet a further aspect, hydrogenation zone 265 may have a pressure in a range of about from 360 psig to about 615 psig (about 2.48 MPag to about 4.24 MPag). In some aspects, an amount of acetylene remaining in the ethylene stream 270 may be less than about 5 ppm by weight; alternatively, in a range of from about 0.5 ppm to about 3 ppm by weight.

Alternatively, all or a portion of the $C_{2-}$ stream 260 is routed through line 266 with valves in streams 260 and 268 and flows into second compression zone 267 to produce a pressurized $C_{2-}$ stream 268. The pressurized $C_{2-}$ stream 268 may have a pressure in a range of from about 100 psig to about 750 psig (about 0.68 MPag to about 5.17 MPag); alternatively, from about 200 psig to about 650 psig (about 1.37 MPag to about 4.48 MPag). Second compression zone 267 comprises one or more gas compressors, wherein the gas compressors may be any gas compressor suitable for use as disclosed herein. The pressurized $C_{2-}$ stream 268 flows into hydrogenation zone 265 wherein a portion of the acetylene comprising the pressurized $C_{2-}$ stream 268 is removed (e.g., via selective hydrogenation to ethylene). The ethylene stream 270 is recovered from hydrogenation zone 265 as disclosed herein.

In another alternative, all or a portion of the effluent of drying zone 245 is an alternate gas stream 272. The alternate gas stream 272 flows into alternate hydrogenation zone 275 wherein a portion of the acetylene comprising the alternate gas stream 272 is removed to produce a reduced gas stream 276. In an aspect, alternate hydrogenation zone 275 operates comparably to hydrogenation zone 265. The reduced gas stream 276 flows into alternate deethanizer zone 277 wherein an alternate ethylene stream 280 is recovered and an alternate $C_{3+}$ stream 282 is produced. In an aspect, alternate deethanizer zone 277 operates comparably to deethanizer zone 255. In a further aspect, the compositions of the alternate ethylene stream 280 and the alternate $C_{3+}$ stream 282 are comparable to the compositions of the ethylene stream 270 and the $C_{3+}$ stream 262, respectively. In an aspect, the alternate $C_{3+}$ stream 282 may be combined with hydrocarbon recycle stream 201. The ethylene stream 270 and/or the alternate ethylene stream 280 flows into a cracking process effluent 25.

III.A.3. Effluent Composition

In an aspect, the cracking process effluent 25 comprises ethylene. An amount of ethylene in the cracking process effluent 25 may be in a range of from about 30 wt. % to about 95 wt. %; alternatively, about 30 wt. % to about 70 wt. %;

or alternatively, about 40 wt. % to about 60 wt. %, based upon a total weight of the cracking process effluent 25.

III.B. Oligomerization Process 300

Returning to FIG. 1, the cracking process effluent 25 flows into oligomerization process 300 wherein monomers (e.g., ethylene) are converted into oligomers (e.g., 1-hexene). In an aspect, the cracking process effluent 25 flows continuously out of cracking process 200 and into oligomerization process 300. One having ordinary skill in the art will appreciate that, as presently described for the cracking process effluent 25, each stream described throughout the present disclosure flows continuously from one process to the next. The continuous flow of each stream is not explicitly stated for the sake of simplicity, but is a feature of each stream. Oligomerization process 300 may comprise a trimerization process whereby an ethylene monomer is contacted with an oligomerization catalyst in an oligomerization reactor to produce a 1-hexene oligomer. In an aspect, the trimerization process comprises a trimerization reaction. For the purposes of the present disclosure the terms oligomerization and trimerization are used interchangeably. Oligomerization process 300 may comprise any trimerization process and/or trimerization reaction suitable for producing 1-hexene as disclosed herein. Methods of converting ethylene into 1-hexene utilizing an oligomerization catalyst system are disclosed in U.S. Pat. No. 7,157,612 which is incorporated herein by reference in its entirety.

Optionally, the cracking process effluent 25 may be further divided into an ethylene feed 27 and/or a utility ethylene stream 29. The ethylene feed 27 comprising ethylene flows into derivatization process 500. The utility ethylene stream 29 comprising ethylene may be routed to storage or for sale.

III.B.1 Flowscheme (1/2)

Figure 3:
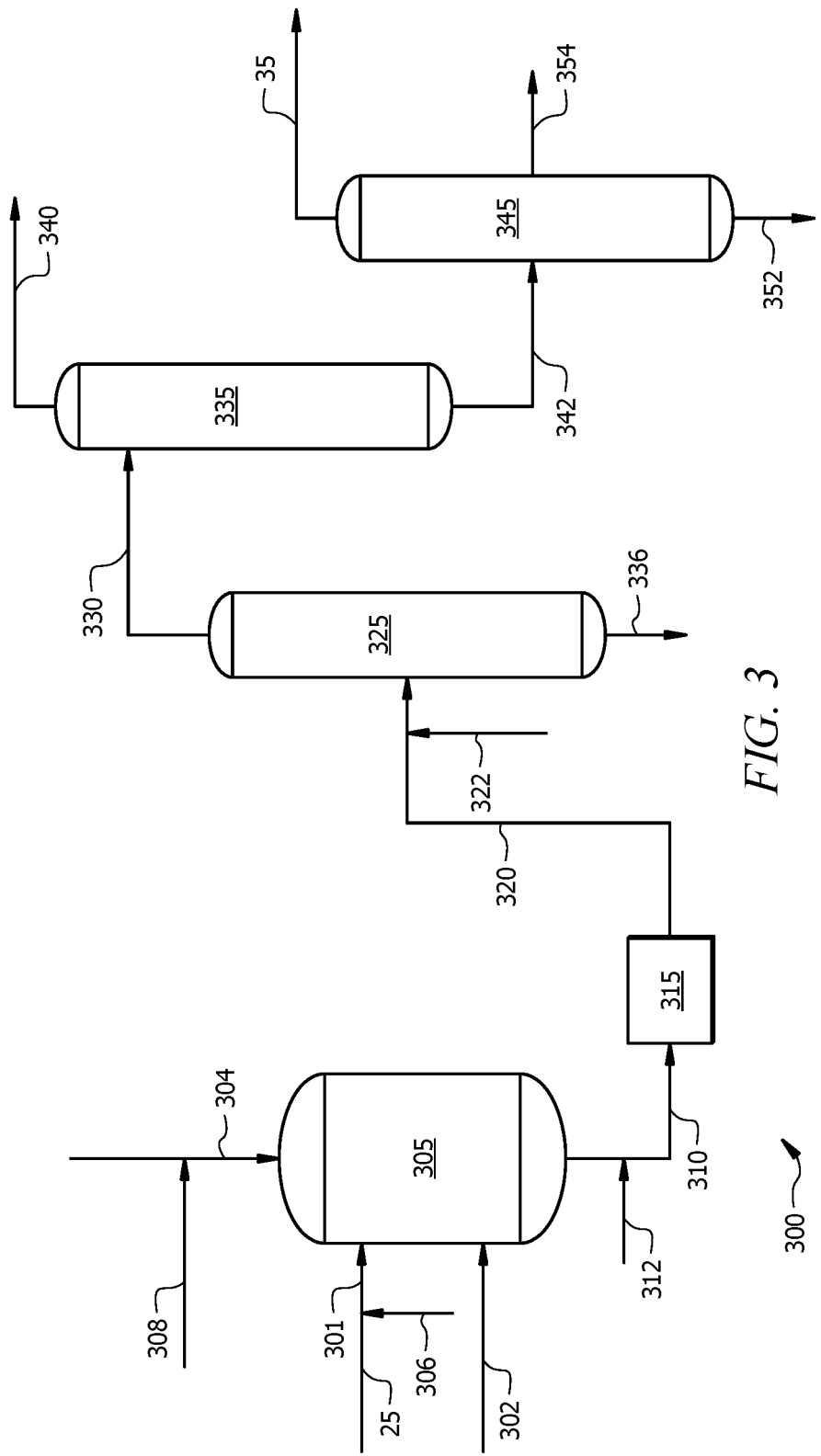
FIG. 3 illustrates a schematic of an oligomerization process.

Referring to FIG. 3, an aspect of oligomerization process 300 is described. The cracking process effluent 25 optionally may be combined with an ethylene recycle stream 306 to form an oligomerization feed stream 301. In an aspect, the ethylene recycle stream 306 may be combined with one or more streams selection from the group consisting of an ethylene effluent 340; a $C_2$ effluent 488 of FIG. 4; an ethylene split stream 165 of FIG. 9; and combinations thereof, as further described herein. In a further aspect, the ethylene recycle stream 306 comprises a light effluent of a polyethylene polymerization process. It is contemplated that some aspects of oligomerization process 300 may operate without the ethylene recycle stream 306. The oligomerization feed stream 301 flows into oligomerization reactor 305. In an aspect, the oligomerization feed stream 301 comprises ethane, ethylene or a combination thereof. A first hydrogen feed stream 302 flows into oligomerization reactor 305. The hydrogen feed stream 302 may be fed to the oligomerization reactor 305 as a separate feed stream, or may be combined with oligomerization feed stream 301 and fed to the oligomerization reactor as a combined feed stream. In an aspect, the first hydrogen feed stream 302 may be combined with a stream from another section of an integrated reforming system of the present disclosure. For example, the first hydrogen feed stream 302 may be combined with one or more streams selected from the group consisting of a hydrogen effluent 41 of FIG. 4; an efflux hydrogen stream 537 of FIG. 5; and combinations thereof, as further described herein. Without wishing to be limited by theory, performing an oligomerization reaction in the presence of hydrogen may enhance product selectivity, reduce formation of polymeric products, or both. It is contemplated that some aspects of oligomerization process 300 may operate without the first hydrogen feed stream 302.

Figure 10:
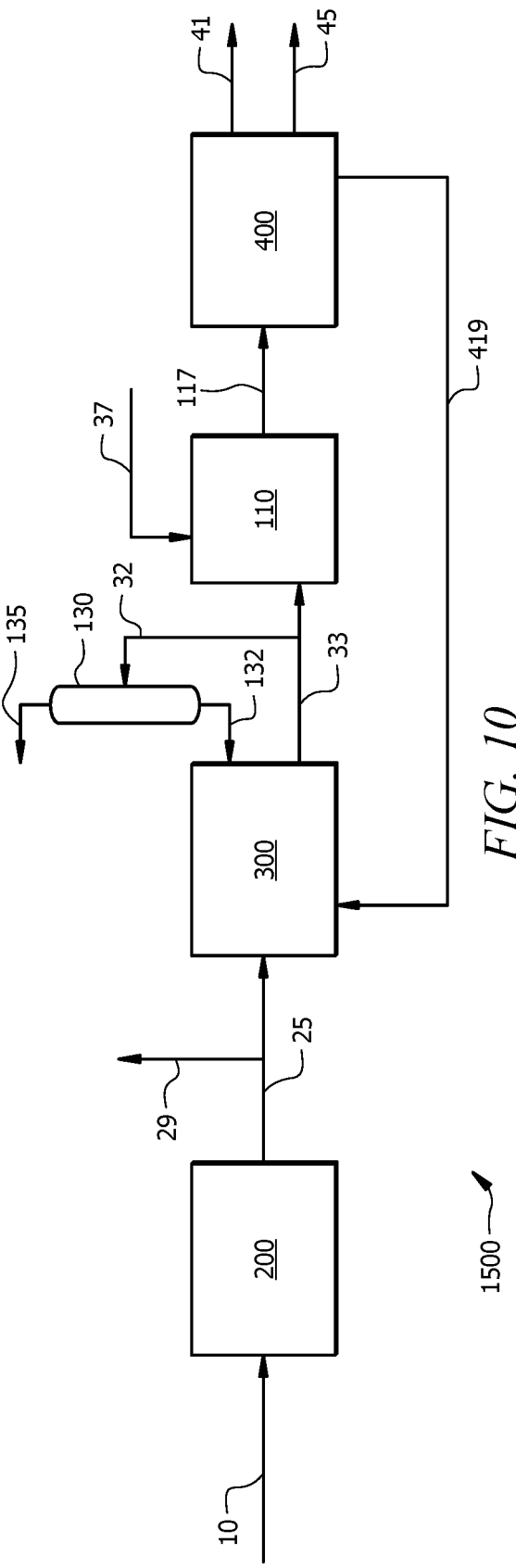
FIG. 10 illustrates a schematic of another integrated converting system.

In an aspect of oligomerization process 300 ethylene is contacted with an oligomerization catalyst in oligomerization reactor 305 in the presence of a solvent. In such aspect, a solvent feed 308 is combined with an oligomerization catalyst stream 304. For the purposes of the present disclosure, "solvent" refers to a diluent or a medium in which the oligomerization reaction occurs. The solvent may be any inert solvent suitable for use in an oligomerization reaction as disclosed herein. In an aspect, the solvent is not necessarily an inert material, and the solvent may participate in the oligomerization. In a further aspect, the solvent may be n-alkanes, branched alkanes, an iso-paraffin, a paraffin, a cycloparaffin, an aromatic hydrocarbon, or combinations thereof. In a further aspect, the solvent may be isobutane, cyclohexane, methylcyclohexane, 2,2,4-trimethylpentane, or combinations thereof. In an aspect where 1-hexene is the product of the oligomerization reaction, the 1-hexene formed therein (i.e., the reaction product) may also serve as the solvent and in such aspect, the oligomerization reaction may be termed a "solventless" oligomerization reaction. Alternatively, in an aspect where 1-hexene is the product of the oligomerization reaction, the solvent is cyclohexane. In an aspect, the solvent feed 308 may be combined with one or more streams selected from the group consisting of a solvent effluent 354; a cyclohexane recycle stream 123 of FIG. 7; with a raffinate stream 419 of FIG. 10; and combinations thereof, as further disclosed herein. It is contemplated that some aspects of oligomerization process 300 may operate without the solvent feed 308.

III.B.2. Catalyst System

The oligomerization catalyst stream 304 flows into oligomerization reactor 305. Oligomerization catalyst systems suitable for the trimerization of ethylene to 1-hexene are described in U.S. Pat. No. 7,157,612 as disclosed herein. In an aspect, an oligomerization catalyst system of the present disclosure comprises a chromium source, a pyrrole-containing compound and a metal alkyl, all of which have been contacted and/or reacted in the presence of an unsaturated hydrocarbon. Optionally, the oligomerization catalyst system may be supported on an inorganic oxide support.

The chromium source can be one or more organic or inorganic compounds, wherein the chromium oxidation state is from 0 to 6. Generally, the chromium source will have a formula of $CrX_n$, wherein X can be the same or different and can be any organic or inorganic radical, and n is an integer from 1 to 6. In an aspect, the organic radicals may have from about 1 to about 20 carbon atoms per radical, and are selected from the group consisting of alkyl, alkoxy, ester, ketone, and/or amido radicals. The organic radicals may be straight-chained or branched, cyclic or acyclic, aromatic or aliphatic, may be made of mixed aliphatic, aromatic, and/or cycloaliphatic groups. In a further aspect, the inorganic radicals include, but are not limited to halides, sulfates, and/or oxides.

In an aspect, the chromium source is a chromium (II)- and/or chromium (III)-containing compound which can yield a catalyst system with trimerization activity suitable for use herein. In a further aspect, the chromium source is a chromium (III) compound because of ease of use, availability, and enhanced catalyst system activity. Non-limiting examples of chromium (III) compounds suitable for use in the present disclosure include chromium carboxylates, chromium naphthenates, chromium halides, chromium pyrrolides, and/or chromium dionates. In an aspect, the chromium (III) compound may be chromium (III) 2,2,6,6,-tetramethylheptanedionate [$Cr(TMHD)_3$], chromium (III) 2-ethylhexanoate [$Cr(EH)_3$, also referred to as chromium (III) tris(2-ethylhexanoate),] chromium (III) naphthenate [Cr(NP)$_3$], chromium (III) chloride, chromic bromide, chromic fluoride, chromium (III) acetylacetonate, chromium (III) acetate, chromium (III) butyrate, chromium (III) neopentanoate, chromium (III) laurate, chromium (III) stearate, chromium (III) oxalate, or combinations thereof. In a further aspect, the chromium (III) compound may be a chromium (III) pyrrolide.

Non-limiting examples of chromium (II) compounds suitable for use in the present disclosure include chromous bromide, chromous fluoride, chromous chloride, chromium (II) bis(2-ethylhexanoate), chromium (II) acetate, chromium (II) butyrate, chromium (II) neopentanoate, chromium (II) laurate, chromium (II) stearate, chromium (II) oxalate, or combinations thereof. In a further aspect, the chromium (II) compound may be a chromium (II) pyrrolide.

The pyrrole-containing compound may be any pyrrole-containing compound, or pyrrolide, that will react with a chromium source to form a chromium pyrrolide complex. As used in this disclosure, the term "pyrrole-containing compound" may refer to hydrogen pyrrolide, (i.e., pyrrole (C$_4$H$_5$N)), derivatives of hydrogen pyrrolide, substituted pyrrolides, or metal pyrrolide complexes. As used in this disclosure, the term "pyrrolide" refers to a 5-membered, nitrogen-containing heterocycle, such as for example, pyrrole, derivatives of pyrrole, and mixtures thereof. Broadly, the pyrrole-containing compound may be pyrrole and/or any heteroleptic or homoleptic metal complex or salt, containing a pyrrolide radical, or ligand. The pyrrole-containing compound may be either affirmatively added to the reactor, or generated in-situ.

Generally, the pyrrole-containing compound will have from about 4 to about 20 carbon atoms per molecule. In an aspect, a pyrrolide suitable for use in the present disclosure may be selected from the group consisting of hydrogen pyrrolide (pyrrole), lithium pyrrolide, sodium pyrrolide, potassium pyrrolide, cesium pyrrolide, and/or the salts of substituted pyrrolides, because of high reactivity and activity with the other reactants. Examples of substituted pyrrolides suitable for use include, but are not limited to, pyrrole-2-carboxylic acid, 2-acetylpyrrole, pyrrole-2-carboxyaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrole-proprionate, ethyl-3,5-dimethyl-2-pyrrolecarboxylate, or combinations thereof. When the pyrrole-containing compound contains chromium, the resultant chromium compound can be called a chromium pyrrolide.

In an aspect, the pyrrole-containing compounds used in the catalyst system are selected from the group consisting of hydrogen pyrrolide, i.e., pyrrole (C$_4$H$_5$N), 2,5-dimethylpyrrole and/or chromium pyrrolides, all of which may provide enhanced trimerization activity. Optionally, for ease of use, a chromium pyrrolide can provide both the chromium source and the pyrrole-containing compound. As used in this disclosure, when a chromium pyrrolide is used to form the catalyst system, a chromium pyrrolide is considered to provide both the chromium source and the pyrrole-containing compound. While all pyrrole-containing compounds may produce catalyst systems with high activity and productivity, use of pyrrole and/or 2,5-dimethylpyrrole may produce a catalyst system desirable levels of activity and selectivity to one or more desired products.

In an aspect, the metal alkyl comprises a heteroleptic or homoleptic metal alkyl compound. In a further aspect, any heteroleptic or homoleptic metal alkyl suitable for use as described herein may be utilized. In a further aspect, one or more metal alkyls may be used. The alkyl ligand(s) on the metal may be aliphatic and/or aromatic. In a further aspect, the alkyl ligand(s) may be any saturated or unsaturated aliphatic radical. The metal alkyl may have any number of carbon atoms. However, due to commercial availability and ease of use, the metal alkyl will usually comprise less than about 70 carbon atoms; alternatively, less than 20 carbon atoms per metal alkyl molecule. Non-limiting examples of metal alkyls suitable for use herein include, alkylaluminum compounds, alkylboron compounds, alkyl magnesium compounds, alkyl zinc compounds and/or alkyl lithium compounds. In a further aspect, the metal alkyl comprises n-butyl lithium, s-butyllithium, t-butyllithium, diethylmagnesium, diethylzinc, triethylaluminum, trimethylaluminum, triisobutylalumium, or combinations thereof.

In a further aspect, the metal alkyl may be a non-hydrolyzed metal alkyl, i.e., not pre-contacted with water. In some aspects, the metal alkyl may be selected from the group consisting of non-hydrolyzed alkylaluminum compounds, non-hydrolyzed derivatives of alkylaluminum compounds, non-hydrolyzed halogenated alkylaluminum compounds, or combinations mixtures thereof. In a further aspect, use of the non-hydrolyzed metal alkyl may improve product selectivity and/or, catalyst system reactivity, activity, and/or productivity. Without wishing to be limited by theory, the use of hydrolyzed metal alkyls can result in decreased olefin, (i.e., liquids), production and increased polymer, (i.e., solids), production.

In an aspect, the metal alkyl comprises a non-hydrolyzed alkylaluminum compound, expressed by the general formulae AlR$_3$, AlR$_2$X, AlRX$_2$, AlR$_2$OR, AlRXOR, and/or Al$_2$R$_3$X$_3$, wherein R is an alkyl group and X is a halogen atom. Non-limiting examples of metal alkyls suitable for use herein include triethylaluminum, tripropylaluminum, tributylaluminum, diethylaluminum chloride, diethylaluminum bromide, diethylaluminum ethoxide, diethylaluminum phenoxide, ethylaluminum dichloride, ethylaluminum sesquichloride, or combinations thereof. In a particular aspect, the alkylaluminum compound may be triethylaluminum.

In a further aspect, an unsaturated hydrocarbon is present during contacting and/or reacting of the chromium source, the pyrrole-containing compound and the metal alkyl, wherein contacting and/or reacting may be performed in any manner suitable for the purposes of the present disclosure. For example, the pyrrole-containing compound can be contacted with the chromium source and then with the metal alkyl. Optionally, the pyrrole-containing compound can be contacted with the metal alkyl and then with the chromium source. Numerous other contacting procedures can be used, such as for example, contacting all oligomerization catalyst system components in oligomerization reactor 305.

The unsaturated hydrocarbon may be any aromatic or aliphatic hydrocarbon, in a gas, liquid or solid state. In an aspect, the unsaturated hydrocarbon in a liquid state effects thorough contacting of the chromium source, the pyrrole-containing compound, and the metal alkyl. The unsaturated hydrocarbon can have any number of carbon atoms per molecule. The unsaturated hydrocarbon may comprise less than about 70 carbon atoms; alternatively, less than 20 carbon atoms per metal alkyl molecule, due to commercial availability and ease of use. Non-limiting examples of unsaturated, aliphatic hydrocarbons suitable for use herein include ethylene, 1-hexene, 1,3-butadiene, or combinations thereof. In an aspect, the unsaturated aliphatic hydrocarbon may be 1-hexene which may be produced within the oligomerization reactor. Without wishing to be limited by theory, aromatic hydrocarbons may improve the stability, the activity, and/or the selectivity of the catalyst system. Non-limiting examples of aromatic hydrocarbons suitable for use herein include toluene, benzene, xylene, ethylbenzene, mesitylene, hexamethylbenzene, or combinations thereof. In an aspect, the aromatic hydrocarbon may be toluene or ethylbenzene; alternatively, toluene; or alternatively, ethylbenzene.

In a particular aspect, the oligomerization catalyst system may optionally comprise a halide source. Without wishing to be limited by theory, the presence of a halide source may improve the stability, the activity, and/or the selectivity of the oligomerization catalyst system. The halide source can be any compound containing a halogen. For example, the halide source may comprise fluoride, chloride, bromide, iodide, or combinations thereof. In a further aspect, the halide source may be chloride or bromide; alternatively, chloride; or alternatively, bromide.

Non-limiting examples of a halide source suitable for use herein include compounds with a general formula of $R_mX_n$, wherein R can be any organic and/or inorganic radical, X can be a halide, selected from the group consisting of fluoride, chloride, bromide, and/or iodide, and m+n can be any number greater than 0. When R is an organic radical, R has from about 1 to about 70 carbon atoms per radical; alternatively, from 1 to 20 carbon atoms per radical. When R is an inorganic radical, R may be selected from the group consisting of aluminum, silicon, germanium, hydrogen, boron, lithium, tin, gallium, indium, lead, or combinations thereof. In an aspect, the halide source may be methylene chloride, chloroform, benzylchloride, silicon tetrachloride, tin(II) chloride, tin(IV) chloride, germanium tetrachloride, boron trichloride, aluminum tribromide, aluminum trichloride, 1,4-di-bromobutane, 1-bromobutane or combinations thereof. In a further aspect, the halide source may be a tin (IV) halide, a germanium halide, or a combination thereof.

In a still further aspect, the halide source may be provided by the chromium source, the metal alkyl, the unsaturated hydrocarbon, or combinations thereof. In an aspect, the halide source may be an alkylaluminum halide used in conjunction with an alkylaluminum compound. Non-limiting examples of alkylaluminum halides suitable for use as the halide source include but are not limited to diisobutyl-aluminum chloride, diethylaluminum chloride, ethylaluminum sesquichloride, ethylaluminum dichloride, diethylaluminum bromide, diethylaluminum iodide, or combinations thereof.

One having ordinary skill in the art will appreciate that a reaction mixture comprising the chromium source, the pyrrole-containing compound, the metal alkyl, the unsaturated hydrocarbon and the optional halide source may further comprise additional components which do not adversely affect, and may enhance, the oligomerization catalyst system as disclosed herein.

III.B.2.a. Catalyst Component Ratios

In an aspect, the oligomerization catalyst system comprises a molar ratio of pyrrole-containing compound to chromium in the chromium source in a range of from about 1:1 to about 80:1; alternatively, about 3:1 to about 50:1; or alternatively, about 10:1 to about 20:1. In a further aspect, the molar ratio of pyrrole-containing compound to chromium in the chromium source may be about 16:1; or alternatively, about 3:1. In yet a further aspect, the oligomerization catalyst system comprises a molar ratio of metal alkyl to chromium in the chromium source in a range of from about 5:1 to about 200:1; alternatively, about 10:1 to about 100:1; or alternatively, about 40:1 to about 60:1. In an aspect, the molar ratio of metal alkyl to chromium in the chromium source may be about 50:1; or alternatively, about 11:1. In a still further aspect, the oligomerization catalyst system comprises a molar ratio of halide source to chromium in the chromium source in a range of from about 2:1 to about 300:1; alternatively, about 5:1 to about 200:1; or alternatively, about 50:1 to about 80:1. In an aspect, the molar ratio of halide source to chromium in the chromium source may be about 63:1; or alternatively, about 8:1.

III.B.3. Oligomerization Reactor Conditions

Within oligomerization reactor 305 contacting of ethylene and an oligomerization catalyst system may occur in any manner suitable and with the aid of the present disclosure. In an aspect, contacting of ethylene and the oligomerization catalyst system may occur by solution reaction, slurry reaction, gas phase reaction, or combinations thereof. In a particular aspect, a suspension formed between the oligomerization catalyst system and a solvent may be agitated to maintain a uniform oligomerization catalyst system concentration throughout the suspension; or alternatively, a solution formed between the oligomerization catalyst system and a solvent may be agitated to maintain the oligomerization catalyst system in solution throughout the oligomerization process. The temperature within oligomerization reactor 305 may be any temperature suitable for a trimerization reaction of ethylene. In an aspect, the temperature is in range that is low enough to avoid decreases in the activity of the oligomerization catalyst system and high enough to avoid formation and/or precipitation of polymeric products. In a further aspect, the temperature within oligomerization reactor 305 may be in a range of from about 0° C. to about 300° C.; alternatively, from about 60° C. to about 275° C.; or alternatively, from about 110° C. to about 125° C. The pressure within oligomerization reactor 305 may be any pressure suitable for a trimerization reaction of ethylene. In an aspect, the pressure is in range that is high enough to avoid decreases in activity of the oligomerization catalyst system. In a further aspect, the pressure within oligomerization reactor 305 may be in a range of from about atmospheric to about 2500 psig (about 0.101 MPag to about 17.24 MPag). When using 1-hexene as the diluent, the pressure may be in a range of from about atmospheric to about 2000 psig (about 0.101 MPag to about 13.79 MPag); alternatively, from about 1100 psig to about 1600 psig (about 7.58 MPag to about 11.03 MPag). When using a diluent other than 1-hexene, the pressure may be in a range of from about atmospheric to about 1500 psig (about 0.101 MPag to about 10.34 MPag); alternatively, from about 600 psig to about 1000 psig (about 4.13 MPag to about 6.9 MPag).

III.B.4. Flowscheme (2/2)

Returning to FIG. 3, an oligomerization reactor effluent stream 310 flowing from oligomerization reactor 305 comprises all components that can be present in and can be removed from an oligomerization reactor. The oligomerization reactor effluent stream 310 may comprise oligomerization product(s), by-product(s), co-product(s), side-product (s), light hydrocarbons, heavy hydrocarbons, unreacted monomer(s), catalyst system, solvent and other reactor components. In an aspect, the oligomerization reactor effluent stream 310 comprises 1-hexene, cyclohexane and unreacted ethylene; or alternatively, 1-hexene and unreacted ethylene. It will be appreciated by one having skill in the art that streams 301, 302, 304, and 310 may be located anywhere on oligomerization reactor 305 suitable to allow the ethylene to thoroughly contact the oligomerization catalyst system within oligomerization reactor 305. A catalyst kill stream 312 is combined the oligomerization reactor effluent stream 310. The catalyst kill stream 312 comprises a catalyst deactivation composition that may deactivate, either partially or completely, the oligomerization catalyst system as disclosed herein. It is contemplated that some aspects of oligomerization process 300 may not utilize the catalyst kill stream 312. Filter 315 can remove particulates (e.g., catalyst fines and undesirable polymeric products) from the oligomerization reactor effluent stream 310. While not wishing to be bound by theory, it is believed that higher reactor and stream temperatures can inhibit solidification of undesirable polymer particles. When the oligomerization reactor effluent stream 310 is maintained at high temperature, fewer particulates can form and filter 315 may be unnecessary. In aspects where process conditions favor particulate formation (e.g., cooling of the oligomerization reactor effluent stream 310), filter 315 can be used. It is contemplated that some aspects of oligomerization process 300 may not utilize filter 315. The process stream 320 comprises the effluent of filter 315 or a continuation of the oligomerization reactor effluent stream 310 wherein the process stream 320 comprises little or no particulates.

The process stream 320 flows into a first separator 325 to produce a light effluent 330 and a heavies effluent 336. The heavies effluent 336 comprises heavy hydrocarbons and the oligomerization catalyst system. The light effluent 330 may comprise 1-hexene, unreacted ethylene, undesired oligomerization products, solvent, and combinations thereof. In an aspect, the light effluent 330 comprises methane, ethane, ethylene, propane, propylene, butane, or combinations thereof. In a further aspect, the first separator 325 comprises a washing process that facilitates removal of the oligomerization catalyst system from the light effluent 330 (e.g., 1-hexene). For the purposes of the present disclosure heavies present in heavies effluent 336 may comprise $C_{8+}$ hydrocarbons, $C_{8+}$ oligomers formed by the oligomerization, polymeric products or combinations thereof. In an aspect, the $C_{8+}$ oligomers formed by the oligomerization reaction include octenes, decenes, dodecenes and tetradecenes. The terms heavies and heavy hydrocarbons are used interchangeably throughout the present disclosure. In an aspect, the heavies effluent 336 may be combined with hydrocarbon recycle stream 201 of FIG. 2 as disclosed herein. In an aspect, a heavies feed 322 is an optional inlet into the first separator 325. The heavies feed 322 may comprise the desired 1-hexene product and/or a heavies component as described herein. In an aspect, the heavies feed 322 may be an effluent of a polyethylene production plant.

The light effluent 330 flows into a second separator 335 to produce an ethylene effluent 340 and a hexene effluent 342. The ethylene effluent 340 may be combined with the ethylene recycle stream 306. In a further aspect, the ethylene effluent 340 may be routed to storage or for sale, for example alone or in combination with utility ethylene stream 29 of FIG. 2. The hexene effluent 342 flows into a third separator 345 wherein a 1-hexene effluent 35 is recovered. The third separator 345 produces a by-product effluent 352 comprising undesired products of the oligomerization reaction. In an aspect, the by-product effluent 352 may be combined with the hydrocarbon recycle stream 201 of FIG. 2, as disclosed herein. In an aspect, a solvent effluent 354 is recovered from the third separator 345 wherein the solvent may comprise cyclohexane. In an aspect, the third separator 345 facilitates removal of the solvent from the 1-hexene effluent 35. The solvent effluent 354 may be combined with the solvent feed 308 as disclosed herein. The first separator 325, second separator 335, and third separator 345 may operate in any manner suitable for producing the effluents thereof. In a further aspect, each of the first separator 325, second separator 335, and third separator 345 comprise at least one fractionator or distillation column.

Alternatively, some aspects of oligomerization process 300 operate in the absence of one or more of the filter 315, the first separator 325, the second separator 335, and the third separator 345 wherein the 1-hexene effluent 35 may be recovered directly from the oligomerization reactor effluent stream 310. In such aspects, the 1-hexene effluent 35 further comprises any components that may be within the oligomerization reactor effluent stream 310 as disclosed herein.

It is contemplated that oligomerization process 300 may be utilized: 1) with monomers other than ethylene; 2) to produce oligomers other than 1-hexene; and/or 3) to perform oligomerization reactions other than trimerization reactions.

III.B.5. Effluent Composition

In an aspect, the 1-hexene effluent 35 may comprise $C_6$ olefins wherein an amount of $C_6$ olefins may be at least 60 wt. %; alternatively, at least 70 wt. %; alternatively, at least 75 wt. %; alternatively, at least 80 wt. %; alternatively, at least 85 wt. %; or alternatively, at least 90 wt. %, based upon a total weight of the 1-hexene effluent 35. In a further aspect, an amount of $C_6$ olefins in the 1-hexene effluent 35 may be in range of from about 60 wt. % to about 99.9 wt. %; alternatively, from about 70 wt. % to about 99.8 wt. %; alternatively, from about 75 wt. % to about 99.7 wt. %; or alternatively, from about 80 wt. % to about 99.6 wt. %; or alternatively, from about 85 wt. % to about 99.6 wt. %. In a further aspect, the 1-hexene effluent 35 may comprise 1-hexene wherein an amount of 1-hexene may be at least 85 wt. %; alternatively, at least 87.5 wt. % alternatively, at least 90 wt. %; alternatively, at least 92.5 wt. %; alternatively, at least 95 wt. %; alternatively, at least 97 wt. %; or alternatively, at least 98 wt. %. In an aspect, the amount of 1-hexene in the 1-hexene effluent 35 may be in a range of from about 85 wt. % to about 99.9 wt. %; alternatively, about 87.5 wt. % to about 99.9 wt. %; alternatively, about 90 wt. % to about 99.9 wt. %; alternatively, about 92.5 wt. % to about 99.9 wt. %; alternatively, about 95 wt. % to about 99.9 wt. %; alternatively, about 97 wt. % to about 99.9 wt. %; or alternatively, about 98 wt. % to about 99.9 wt. %.

III.C. Aromatization Process 400

Returning to FIG. 1, the 1-hexene effluent 35 flows into aromatization process 400. In an aspect, aromatization process 400 comprises an aromatization reactor system wherein acyclic oligomers are contacted with an aromatization catalyst and undergo thereby an aromatization reaction that produces arenes. In a further aspect, the aromatization reaction converts 1-hexene into benzene. Methods for converting 1-hexene into benzene are disclosed in U.S. Pat. No. 7,932,425 which is incorporated herein by reference in its entirety. Any suitable method of producing benzene disclosed in U.S. Pat. No. 7,932,425 may be utilized herein. It is contemplated that aromatization process 400 may be utilized with acyclic hydrocarbons other than 1-hexene to produce arenes other than benzene.

In an aspect, an auxiliary aromatization feed 37 flows into aromatization process 400. The auxiliary aromatization feed 37 may comprise non-aromatic hydrocarbons containing at least six carbon atoms. In a further aspect, the auxiliary aromatization feed 37 may comprise a mixture of hydrocarbons comprising $C_6$ to $C_8$ hydrocarbons comprising up to about 15 wt. % of $C_{5-}$ hydrocarbons and up to about 10 wt. % of $C_{9+}$ hydrocarbons wherein weight percentage is based upon a total weight of the auxiliary aromatization feed 37. In a particular aspect, the auxiliary aromatization feed 37 may comprise a naphtha feed. In an aspect, the naphtha feed may be a light naphtha with a boiling range of about 70° F.

to about 450° F. (about 21.1° C. to about 232.2° C.), wherein the naphtha feed may contain aliphatic, naphthenic, or paraffinic hydrocarbons. It is contemplated that some aspects of aromatization process 400 may operate without the auxiliary aromatization feed 37.

III.C.1 Flowscheme

III.C.1.a. Reactor System

Figure 4:
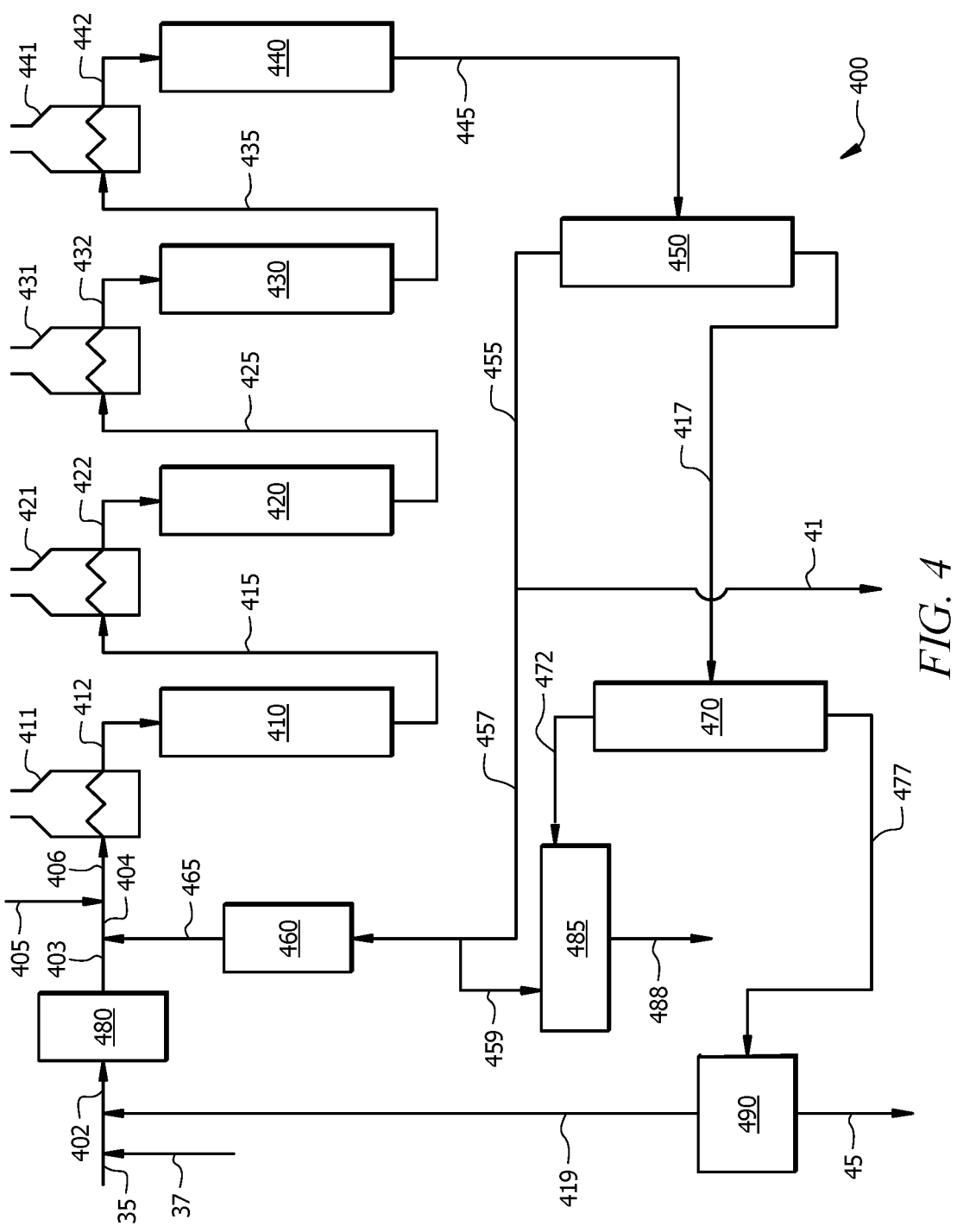
FIG. 4 illustrates a schematic of an aromatization process.

Referring to FIG. 4, an aspect of aromatization process 400 is described. In the aspect shown, the aromatization reactor system comprises a catalytic reactor system wherein four aromatization reactors are serially connected; reactors 410, 420, 430, and 440. However, the catalytic reactor system may comprise any suitable number and configuration of aromatization reactors, for example one, two, three, five, six, or more reactors in series or in parallel. As aromatization reactions are highly endothermic, large temperature drops occur across the reactors 410, 420, 430, and 440. Therefore, each reactor 410, 420, 430, and 440 in the series may comprise a corresponding furnace 411, 421, 431, and 441, respectively, for heating reactor feed components to a desired temperature (e.g., to a temperature associated with a desired reaction rate within a given reactor). Alternatively, one or more reactors 410, 420, 430, and 440 may share a common furnace where practical. All of the reactors 410, 420, 430, and 440, furnaces 411, 421, 431, and 441, and associated piping may be referred to herein as the aromatization zone.

The 1-hexene effluent 35, the auxiliary aromatization feed 37 (when present), and optionally a raffinate stream 419 combine to form a mixed feed stream 402 that flows into purification process 480. Purification process 480 employs known processes to purify the mixed feed stream 402, which may include fractionation or other separation techniques, to remove impurities, such as oxygenates, sulfur, and/or metals. In an aspect, purification process 480 comprises a sulfur removal system. In a further aspect, the sulfur removal system comprises a sulfur guard bed. Emanating from purification process 480 is a purified feed stream 403. The purified feed stream 403 optionally may be combined with a dry hydrogen recycle stream 465 to produce a hydrogen-rich purified feed stream 404. An oxygenate and/or nitrogenate stream 405 (i.e., O/N stream) optionally may be combined with the hydrogen-rich purified feed stream 404 to produce an aromatization reactor feed stream 406. The oxygenate and/or nitrogenate may be fed to the catalytic reactor system at one or more locations in addition to the O/N stream 405 or as an alternative to the O/N stream 405, as described in more detail herein. It is contemplated that some aspects of aromatization process 400 may operate without purification process 480, wherein the mixed feed stream 402 continues directly into stream 403.

The aromatization reactor feed stream 406 is pre-heated in a first furnace 411, which heats the contents of feed stream 406 to a desired temperature, thereby producing a first aromatization reactor feed stream 412. The first aromatization reactor feed stream 412 flows into a first aromatization reactor 410, where it is contacted with an aromatization catalyst under suitable reaction conditions (e.g., temperature and pressure) that aromatize one or more components in the feed (e.g., 1-hexene), thereby increasing the arene content thereof. A first aromatization reactor effluent stream 415 comprising arenes (e.g., benzene), unreacted feed, and optionally other hydrocarbon compounds or byproducts is recovered from the first aromatization reactor 410.

The first aromatization reactor effluent stream 415 is then pre-heated in a second furnace 421, which heats the contents of stream 415 to a desired temperature, thereby producing a second aromatization reactor feed stream 422. The second aromatization reactor feed stream 422 flows into a second aromatization reactor 420, where it is contacted with an aromatization catalyst under suitable reaction conditions for aromatizing one or more components in the feed (e.g., 1-hexene) to increase the arene content thereof. A second aromatization reactor effluent stream 425 comprising arenes (e.g., benzene), unreacted feed, and optionally other hydrocarbon compounds or byproducts is recovered from the second aromatization reactor 420.

The second aromatization reactor effluent stream 425 is then pre-heated in a third furnace 431, which heats the contents of stream 425 to a desired temperature, thereby producing a third aromatization reactor feed stream 432. The third aromatization reactor feed stream 432 flows into a third aromatization reactor 430, where it is contacted with an aromatization catalyst under suitable reaction conditions for aromatizing one or more components in the feed (e.g., 1-hexene) to increase the arene content thereof. A third aromatization reactor effluent stream 435 comprising arenes (e.g., benzene), unreacted feed, and optionally other hydrocarbon compounds or byproducts is recovered from the third aromatization reactor 430.

The third aromatization reactor effluent stream 435 is then pre-heated in a fourth furnace 441, which heats the contents of stream 435 to a desired temperature, thereby producing a fourth aromatization reactor feed stream 442. The fourth aromatization reactor feed stream 442 is then fed into a fourth aromatization reactor 440, where it is contacted with an aromatization catalyst under suitable reaction conditions for aromatizing one or more components in the feed (e.g., 1-hexene) to increase the arene content thereof. A fourth aromatization reactor effluent stream 445 comprising arenes (e.g., benzene), unreacted feed, and optionally other hydrocarbon compounds or byproducts is recovered from the fourth aromatization reactor 440.

III.C.1.b. Downstream Processing

The fourth aromatization reactor effluent stream 445 flows into a hydrogen separation process 450 wherein a recovered hydrogen stream 455 is separated from a first reformate stream 417. The first reformate stream 417 comprises the aromatization reaction products from reactors 410, 420, 430, and 440; and optionally, aromatization reaction by-product(s) and/or side-product(s), unreacted feed, other hydrocarbons or combinations thereof. In an aspect, the aromatization reaction side-products comprise toluene, xylene, ethylbenzene, diethylbenzene, mesitylene, hexamethylbenzene, or combinations thereof. The first reformate stream 417 flows into a reformate purification process 470 wherein a second reformate 477 is separated from a light reformate effluent 472. In an aspect, the light reformate effluent 472 comprises $C_{5-}$ hydrocarbons. The second reformate 477 flows into a purification-extraction process 490 wherein a benzene effluent 45 is recovered. The purification-extraction process 490 produces a raffinate stream 419 and, optionally, a stream comprising aromatization reaction by-product(s) and/or side-product(s). In an aspect, the raffinate stream 419 may comprise benzene, toluene, xylene, branched alkanes, or a combination thereof. In an aspect, the raffinate stream 419 is recycled and combined with the mixed feed stream 402 as disclosed herein. The recovered hydrogen stream 455 may be split from 0% to 100% between a hydrogen recycle stream 457 and a hydrogen effluent 41. In an aspect, the hydrogen effluent 41 may be combined with the first hydrogen feed stream 302 of FIG. 3 as disclosed herein. In a further aspect, the hydrogen effluent 41 may be routed to storage or for sale. A first portion of the hydrogen recycle stream 457 is routed into a second hydrogen feed 459. A second portion of the hydrogen recycle stream 457 is dried in dryer 460, forming a dry hydrogen recycle stream 465 thereby, which may be recycled into the purified feed stream 403 as disclosed herein.

The second hydrogen feed 459 and the light reformate effluent 472 comprising $C_{5-}$ hydrocarbons enter $C_2$ recovery zone 485. In an aspect, $C_2$ recovery zone 485 comprises a demethanizer; alternatively, a depropanizer; alternatively, a demethanizer upstream from a depropanizer, or alternatively, a demethanizer downstream from a depropanizer. A $C_2$ effluent 488 flows out of $C_2$ recovery zone 485. In an aspect, the $C_2$ effluent 488 comprises ethane, ethylene or a combination thereof and may be combined with the hydrocarbon recycle stream 201 of FIG. 2, the ethylene recycle stream 306 of FIG. 3, or both.

The hydrogen separation process 450 and purification-extraction process 490 may be employed, for example as described in U.S. Pat. Nos. 5,401,386; 5,877,367; and 6,004,452, each of which is incorporated herein by reference in its entirety. For the sake of simplicity, FIG. 4 does not illustrate the byproduct streams that are removed from the catalytic reactor system at various points throughout the system. However, persons of ordinary skill in the art are aware of the composition and location of such byproduct streams. Also, while FIG. 4 shows the O/N stream 405 being added to the hydrogen-rich purified feed stream 404, persons of ordinary skill in the art will appreciate that the oxygenate and/or nitrogenate may be added to any of streams 402, 403, 404, 406, 412, 415, 417, 419, 422, 425, 432, 435, 442, 445, 455, 465, 457, or combinations thereof.

III.C.2 Process Detail

In various aspects, the catalytic reactor system described herein may comprise a fixed catalyst bed system, a moving catalyst bed system, a fluidized catalyst bed system, or combinations thereof. In an aspect, the catalytic reactor system is a fixed bed system comprising one or more fixed bed reactors. In a fixed bed system, the aromatization reactor feed may be preheated in furnace tubes and passed into at least one reactor that contains a fixed bed of the catalyst. The flow of the aromatization reactor feed can be upward, downward, or radially through the reactor. In various aspects, the catalytic reactor system described herein may be operated as an adiabatic catalytic reactor system or an isothermal catalytic reactor system. As used herein, the term "catalytic reactor" and "reactor" refer interchangeably to the reactor vessel, reactor internals, and associated processing equipment, including but not limited to the catalyst, inert packing materials, scallops, flow distributors, center pipes, reactor ports, catalyst transfer and distribution system, furnaces and other heating devices, heat transfer equipment, and piping.

In an aspect, the catalytic reactor system is an aromatization reactor system comprising at least one aromatization reactor and its corresponding processing equipment. As used herein, the terms "aromatization," "aromatizing," and "reforming" refer to the treatment of a feed to provide an arene-enriched product wherein an arene content of the product is greater than that of the feed. Typically, one or more components of the feed undergo one or more reforming reactions to produce arenes. Some of the reforming reactions that occur within the aromatization reactor system include dehydrocyclization reactions of acyclic hydrocarbons to arenes (e.g., 1-hexene to benzene), dehydrogenation reactions of cyclohexanes to arenes, dehydroisomerization reactions of alkylcyclopentanes to arenes, or combinations thereof. Depending upon the composition of the feed, a number of other reactions may also occur, including dealkylation reactions of alkylbenzenes, isomerization reactions of paraffins, hydrocracking reactions that produce light gaseous hydrocarbons, e.g., methane, ethane, ethylene, propane propylene, and butane, or combinations thereof. Particular aspects of the integrated reforming systems described herein utilize dehydrocyclization reactions of 1-hexene, n-hexane or a combination thereof to produce benzene. In a further aspect, the integrated reforming systems utilize dehydrogenation reactions of cyclohexane produce benzene.

In an aspect, the aromatization reaction occurs under process conditions that thermodynamically favor the dehydrocyclization reaction and limit undesirable hydrocracking reactions. Pressures within the reactor(s) may be in a range of from about 0 psig to about 500 psig (about 0 MPag to about 3.45 MPag), alternatively about 25 psig to about 300 psig (about 0.17 MPag to about 2.07 MPag). The operating temperatures include reactor inlet temperatures in a range of from about 370° C. to about 565° C., alternatively about 480° C. to about 540° C. A molar ratio of hydrogen to hydrocarbons (e.g., 1-hexene) in the aromatization reactor feed, may be in a range of from about 0.1:1 to about 20:1, alternatively from about 1:1 to about 6:1.

III.C.2.a. Conversion & Selectivity

The aromatization reaction of the present disclosure may be characterized by a conversion of 1-hexene to benzene based upon a total amount-by-weight of 1-hexene fed to the aromatization reactor. In an aspect, the conversion of 1-hexene to benzene is greater than about 40 wt. %; alternatively, greater than about 50 wt. %; alternatively, greater than about 60 wt. %; or alternatively, greater than about 70 wt. %.

The aromatization reaction of the present disclosure may be characterized by a selectivity of 1-hexene to benzene based upon a total amount-by-weight of 1-hexene converted in the aromatization reactor. In an aspect, the selectivity of 1-hexene to benzene is greater than about 50 wt. %; alternatively, greater than about 60 wt. %; alternatively, greater than about 70 wt. %; or alternatively, greater than about 75 wt. %.

III.C.3. Catalyst

Various types of aromatization catalysts may be used with the catalytic reactor system disclosed herein. In an aspect, the aromatization catalyst is a non-acidic catalyst that comprises an inorganic support, a group VIII metal, and one or more halides. Suitable halides include chloride, fluoride, bromide, iodide, or combinations thereof. Suitable Group VIII metals include iron, cobalt, nickel, ruthenium, rhodium, palladium, osmium, iridium, and platinum. Examples of catalysts suitable for use with the catalytic reactor system described herein are the AROMAX® brand of catalysts available from the Chevron Phillips Chemical Company of The Woodlands, Tex., including the catalysts discussed in U.S. Pat. Nos. 7,932,425; 6,812,180; and 7,153,801, each of which is incorporated herein by reference in its entirety.

Inorganic supports for the aromatization catalyst of the present disclosure may generally include any inorganic oxide. These inorganic oxides include bound large pore aluminosilicates (zeolite supports), amorphous inorganic oxides and mixtures thereof. Large pore aluminosilicates include, but are not limited to, L-zeolite, Y-zeolite, mordenite, omega zeolite, beta zeolite and the like. Amorphous inorganic oxides include, but are not limited to, aluminum oxide, silicon oxide, and titania. Suitable bonding agents for the inorganic oxides include, but are not limited to, silica, alumina, clays, titania, and magnesium oxide.

In an aspect, the support is a bound potassium L-type zeolite, or KL zeolite. The term "KL zeolite" as used herein refers to L-type zeolites in which the principal cation M incorporated in the zeolite is potassium. A KL zeolite may be cation-exchanged or impregnated with another metal and one or more halides to produce a platinum-impregnated, halided zeolite or a KL supported Pt-halide zeolite catalyst.

In an aspect, the Group VIII metal may be platinum. The platinum and optionally one or more halides may be added to the zeolite support by any suitable method, for example via impregnation with a solution of a platinum-containing compound and one or more halide-containing compounds. For example, the platinum-containing compound can be any decomposable platinum-containing compound. Examples of such compounds include, but are not limited to, ammonium tetrachloroplatinate, chloroplatinic acid, diamineplatinum (II) nitrite, bis-(ethylenediamine)platinum (II) chloride, platinum (II) acetylacetonate, dichlorodiamine platinum, platinum (II) chloride, tetraamineplatinum (II) hydroxide, tetraamineplatinum chloride, and tetraamineplatinum (II) nitrate.

In a further aspect, the catalyst may be a large pore zeolite support with a platinum-containing compound and at least one organic ammonium halide compound. The organic ammonium halide compound may comprise one or more compounds represented by the formula $N(R)_4X$, where X is a halide and where R represents a hydrogen or a substituted or unsubstituted carbon chain molecule having 1-20 carbons wherein each R may be the same or different. In an aspect, R is selected from the group consisting of methyl, ethyl, propyl, butyl, and combinations thereof, more specifically methyl. Examples of suitable organic ammonium compounds are represented by the formula $N(R)_4X$ include ammonium chloride, ammonium fluoride, and tetraalkylammonium halides such as tetramethylammonium chloride, tetramethylammonium fluoride, tetraethylammonium chloride, tetraethylammonium fluoride, tetrapropylammonium chloride, tetrapropylammonium fluoride, tetrabutylammonium chloride, tetrabutylammonium fluoride, methyltriethylammonium chloride, methyltriethylammonium fluoride, and combinations thereof.

III.C.4. Oxygenate/Nitrogenate

In a particular aspect of the present disclosure, an oxygenate, a nitrogenate, or both may be added to one or more process streams and/or components in the catalytic reactor system. Not wishing to be limited by theory, the oxygenate and/or nitrogenate (e.g., water) may be beneficial in activating, preserving, and/or increasing the productivity of certain types of aromatization catalysts as described in U.S. Pat. No. 7,932,425. In an aspect, the 1-hexene effluent 35, the auxiliary aromatization feed 37, and the optional raffinate recycle 419 are substantially free of sulfur, metals, and other known poisons for aromatization catalysts, and are initially substantially free of oxygenates and nitrogenates. If present, such poisons can be removed using methods known to those skilled in the art. In some aspects, 1-hexene effluent 35, the auxiliary aromatization feed 37, and the optional raffinate recycle 419 can be purified by first using conventional hydrofining techniques, then using sorbents to remove the remaining poisons. Such hydrofining techniques and sorbents are included in the purification process associated with the oxygenate and/or nitrogenate described below As used herein, the term "oxygenate" refers to water or any chemical compound that forms water under catalytic aromatization conditions, such as oxygen, oxygen-containing compounds, hydrogen peroxide, alcohols, ketones, esters, ethers, carbon dioxide, aldehydes, carboxylic acids, lactones, ozone, carbon monoxide or combinations thereof. In one aspect, water and/or steam is used as the oxygenate.

In another aspect, oxygen may be used as the oxygenate, wherein such oxygen converts to water in situ within one or more aromatization reactors under typical aromatization conditions or within one or more hydrofining catalyst or sorbent beds under normal hydrofining conditions. Furthermore, the oxygenate may be any alcohol-containing compound. Specific examples of suitable alcohol-containing compounds are methanol, ethanol, propanol, isopropanol, butanol, t-butanol, pentanol, amyl alcohol, hexanol, cyclohexanol, phenol, or combinations thereof.

As used herein, the term "nitrogenate" refers to ammonia or any chemical compound that forms ammonia under catalytic aromatization conditions such as nitrogen, nitrogen-containing compounds, alkyl amines, aromatic amines, pyridines, pyridazines, pyrimidines, pyrazines, triazines, heterocyclic N-oxides, pyrroles, pyrazoles, imadazoles, triazoles, nitriles, amides, ureas, imides, nitro compounds, nitroso compounds, or combinations thereof. While not wanting to be limited by theory, it is believed that the ammonia will improve catalyst activity in much the same way as the water. Additionally, all the methods of addition and control for oxygenates described herein can also be fully applied additionally or alternatively to the methods of addition and control for nitrogenates.

Those having ordinary skill in the art will appreciate that any of the oxygenates, nitrogenates, or mixtures thereof described herein may be used alone, in combination, or further combined to produce other suitable oxygenates or nitrogenates. In some aspects, the oxygenate and nitrogenate may be contained within a single bifunctional compound. The oxygenate and/or nitrogenate may be added in any suitable physical phase such as a gas, liquid, or combinations thereof. The oxygenate and/or nitrogenate may be added to one or more process streams and/or components via any suitable means for their addition, for example a pump, injector, sparger, bubbler, or the like. The oxygenate and/or nitrogenate may be introduced as a blend with a carrier. In some aspects, the carrier is hydrogen, a hydrocarbon, nitrogen, a noble gas, or mixtures thereof. In an aspect, the carrier is hydrogen. In a further aspect, the oxygenate and/or nitrogenate may be added at various locations within the aromatization process, at any time during the service life of the aromatization catalyst, and in any suitable manner. In a still further aspect, the addition of oxygenate and/or nitrogenate functions to activate the aromatization catalyst, to increase the useful life of the aromatization catalyst, to increase the selectivity and/or productivity of the aromatization catalyst, and combinations thereof.

In an aspect, the existing oxygenate and/or nitrogenate content of a stream to which the oxygenate and/or nitrogenate is to be added is measured and/or adjusted prior to addition of the oxygenate and/or nitrogenate. For example and with reference to FIG. 4, one or more feed streams such as the 1-hexene effluent 35, the auxiliary aromatization feed 37, the raffinate stream 419, the mixed feed stream 402, or the dry hydrogen recycle stream 465 may be measured for oxygenate and/or nitrogenate content and the oxygenate and/or nitrogenate content thereof adjusted prior to the addition of the oxygenate and/or nitrogenate. Likewise, the same streams may be measured for nitrogenate content and/or the nitrogenate content thereof adjusted prior to the addition of the nitrogenate. Generally, a raw or untreated feed stream such as the 1-hexene effluent 35 may contain some amount of oxygenate or nitrogenate when it flows into the catalytic reaction system described herein. In addition, depending on the plant configuration, the duration of feed storage and weather conditions, the feed may absorb oxygenates or nitrogenates from the air. In order to accurately control the amount of oxygenate or nitrogenates flowing into one or more of the aromatization reactors (e.g., reactors 410, 420, 430, 440), the amount of oxygenate and/or nitrogenate in one or more feed streams to the reactors may be measured, adjusted, or both.

In an aspect, the oxygenate and/or nitrogenate content of a given stream such as a feed stream may be measured, for example with a real-time, in-line analyzer (not shown). In response to such measurement, the oxygenate and/or nitrogenate content of the stream may be adjusted by treating and/or adding oxygenate and/or nitrogenate to the stream to obtain a desired amount of oxygenate and/or nitrogenate therein. In an aspect, a control loop links the analyzer to a treater and an oxygenate and/or nitrogenate injector such that the amount of oxygenate and/or nitrogenate in one or more streams is controlled in response to an oxygenate and/or nitrogenate set point for such streams. In an aspect the measuring and/or adjusting of the oxygenate and/or nitrogenate content and associated equipment such as treaters and/or chemical injectors are included as part of the purification process 480. The oxygenate and/or nitrogenate treaters vary based on the type and amounts of oxygenate and/or nitrogenate. In aspects where the oxygenate comprises water, beds of sorbent materials may be used. These sorbent beds are commonly known as driers. In aspects where the oxygenate comprises oxygen, the use of treaters which convert the oxygen to water can be used in combination with driers. In further aspects where the nitrogenate comprises a basic chemical, beds of sorbent materials may be used.

In an aspect, one or more streams such as the 1-hexene effluent 35, the auxiliary aromatization feed 37, the raffinate stream 419, the mixed feed stream 402, or the dry hydrogen recycle stream 465 are treated prior to the addition of oxygenate and/or nitrogenate thereto. In such an aspect, measuring the oxygenate and/or nitrogenate content of the streams before such treatment may optionally be omitted. If there is no apparatus for readily measuring the oxygenate and/or nitrogenate content of the feed, then it is difficult to reliably maintain a desired level in the aromatization reactors.

Treating one or more streams prior to the addition of the oxygenate and/or nitrogenate may aid in the overall control of the amount of water and/or ammonia in one or more streams flowing into the aromatization reactors by removing variability in the oxygenate and/or nitrogenate content in such streams. Treating such streams provides a consistent, baseline amount of oxygenate and/or nitrogenate in such streams for the addition of oxygenate and/or nitrogenate to form an oxygenated stream such as the aromatization reactor feed stream 406. When the reactor feed is sufficiently free of oxygenates and/or nitrogenates, precise quantities of the oxygenate and/or nitrogenates can be added to the reactor feeds such that the amount of oxygenate and/or nitrogenates in the reactors may be reliably maintained. In an aspect, purification process 480 may include a hydrocarbon dryer that dries the feed streams (e.g., 1-hexene effluent 35), to a suitable moisture content. In other aspects, purification process 480 may include a reduced copper bed or a bed of triethyl aluminum on silica for use in removing oxygenates. In still further aspects, the reduced copper bed or a bed of triethyl aluminum on silica is used in combination with the hydrocarbon dryer. Similarly, dryer 460 can be used to dry the hydrogen recycle stream 457 and/or other process streams (e.g., 1-hexene effluent 35), to a suitable moisture content. In an aspect, a suitable oxygenate level in one or more streams, such as the 1-hexene effluent 35, the auxiliary aromatization feed 37, the raffinate stream 419, the mixed feed stream 402, or the dry hydrogen recycle stream 465, is such that the combination thereof produces a water concentration of less than about 1 ppmv, alternatively less than about 0.5 ppmv, or alternatively less than about 0.1 ppmv in the untreated recovered hydrogen stream 455. In an aspect, one or more streams fed to the aromatization reactors, such as the 1-hexene effluent 35, the auxiliary aromatization feed 37, the raffinate stream 419, the mixed feed stream 402, or the dry hydrogen recycle stream 465, are substantially free of water following drying thereof. In an aspect, the precise amount of the oxygenate and/or the nitrogenate may be added by partially or fully bypassing such treatment processes. Alternatively, the precise amount of the oxygenate and/or the nitrogenate may be added by partially or fully running the hydrogen recycle stream 457 through a wet, e.g. spent, mole sieve bed.

III.C.5. Effluent Composition

The benzene effluent 45 may comprise $C_6$ arenes. In an aspect, an amount of $C_6$ arenes in the benzene effluent 45 may be at least 60 wt. %; alternatively, at least 70 wt. %; alternatively, at least 75 wt. %; alternatively, at least 80 wt. %; alternatively, at least 85 wt. %; or alternatively, at least 90 wt. %, based upon a total weight of the benzene effluent 45. In a further aspect, an amount of $C_6$ arenes in the benzene effluent 45 may be in range of from about 60 wt. % to about 99.9 wt. %; alternatively, from about 70 wt. % to about 99.8 wt. %; alternatively, from about 75 wt. % to about 99.7 wt. %; or alternatively, from about 80 wt. % to about 99.6 wt. %; or alternatively, from about 85 wt. % to about 99.6 wt. %. In a further aspect, an amount of benzene in the benzene effluent 45 may be at least 85 wt. %; alternatively, at least 87.5 wt. % alternatively, at least 90 wt. %; alternatively, at least 92.5 wt. %; alternatively, at least 95 wt. %; alternatively, at least 97 wt. %; or alternatively, at least 98 wt. %, wherein. In an aspect, the amount of benzene in the benzene effluent 45 may be in a range of from about 85 wt. % to about 99.9 wt. %; alternatively, about 87.5 wt. % to about 99.9 wt. %; alternatively, about 90 wt. % to about 99.9 wt. %; alternatively, about 92.5 wt. % to about 99.9 wt. %; alternatively, about 95 wt. % to about 99.9 wt. %; alternatively, about 97 wt. % to about 99.9 wt. %; or alternatively, about 98 wt. % to about 99.9 wt. %.

III.D. Derivatization Process 500

Returning to FIG. 1, the benzene effluent 45 may be routed for storage or for sale. In a further aspect, a portion of the benzene effluent 45 is routed through a benzene feed 47 comprising benzene that flows into derivatization process 500. In a further aspect, derivatization process 500 comprises an ethylbenzene-styrene production process. Processes to produce ethylbenzene and styrene from benzene are disclosed in U.S. Pat. Nos. 5,602,290; 5,880,320; 5,856,607; 6,252,126; and 6,790,342; each of which is incorporated herein by reference in its entirety. It is contemplated that derivatization process 500 may comprise a process other than the ethylbenzene-styrene production process.

III.D.1. Flowscheme

Figure 5:
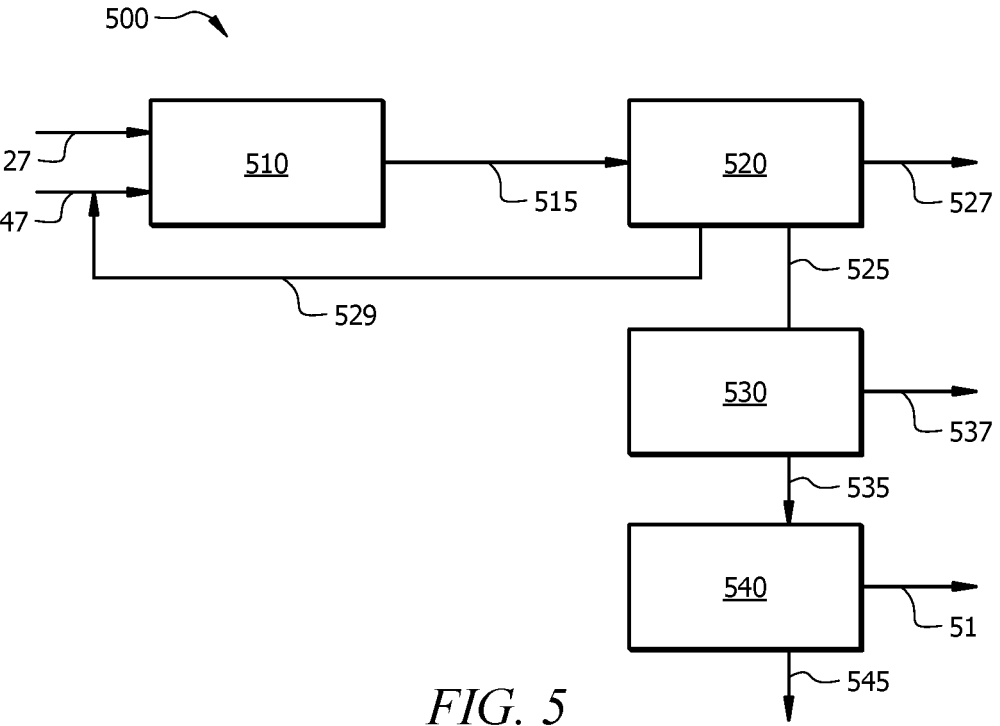
FIG. 5 illustrates a schematic of a derivatization process.

Referring to FIG. 5, aspects of the derivatization process 500 are described. The benzene feed 47 and an ethylene feed 27 flow into alkylation zone 510. In an aspect, alkylation zone 510 comprises at least one alkylation reactor. Benzene and ethylene are contacted with an alkylation catalyst within alkylation zone 510 to produce an alkylation reactor effluent 515. Benzene, ethylene, and the alkylation catalyst may be contacted in any manner suitable for the formation of ethylbenzene. In an aspect, the alkylation catalyst comprises a zeolite catalyst, a non-limiting example of which includes a ZSM-based zeolite. ZSM-based zeolites are aluminosilicate zeolites having a chemical formula of $Na_nAl_nSi_{96-n}O_{192} \cdot 16H_2O$ where n is an integer from between 0 and 27. In a further aspect, the ZSM-based zeolite may impart a selectivity of greater than 99% when used for the formation of ethylbenzene from ethylene and benzene.

In an aspect, the alkylation reactor effluent 515 comprises benzene and ethylbenzene. The alkylation reactor effluent 515 flows into a first separation zone 520 wherein an ethylbenzene stream 525 comprising ethylbenzene is recovered. The first separation zone 520 further produces a polyalkylated stream 527 and a benzene recycle stream 529. The first separation zone 520 may operate in any manner known to one having skill in the art and with the aid of the present disclosure. In a further aspect, the first separation zone 520 comprises at least one fractionator. The polyalkylated stream 527 comprises $C_{10+}$ arenes including, but not limited to, diethylbenzene and triethylbenzene. In an aspect, the polyalkylated stream 527 may be combined with the hydrocarbon recycle stream 201 of FIG. 2 as disclosed herein. The benzene recycle stream 529 is combined with the benzene feed 47.

The ethylbenzene stream 525 flows into dehydrogenation zone 530. In an aspect, dehydrogenation zone 530 comprises at least one dehydrogenation reactor. Within dehydrogenation zone 530 ethylbenzene is contacted with a dehydrogenation catalyst to produce a dehydrogenation reactor effluent 535 and an efflux hydrogen stream 537. In an aspect, the dehydrogenation reactor effluent 535 comprises styrene. Ethylbenzene and the dehydrogenation catalyst may be contacted in any manner suitable for the formation of styrene. The dehydrogenation reactor effluent 535 flows into a second separation zone 540 to form a styrene effluent 51 and an aromatics stream 545. The second separation zone 540 may operate in any manner known to one having skill in the art and with the aid of the present disclosure. In a further aspect, the second separation zone 540 comprises at least one fractionator. The styrene effluent 51 may be routed for storage or for sale. The aromatics stream 545 may comprise $C_{6+}$ arenes including, but not limited to, unreacted ethylbenzene and/or undesired products of the processes occurring in zones 510, 520 and/or 530. In an aspect, the aromatics stream 545 may be combined (not shown), with the polyalkylated stream 527. In a further aspect, the aromatics stream 545 may be combined (not shown), with the hydrocarbon recycle stream 201 of FIG. 2 as disclosed herein. In an aspect, the efflux hydrogen stream 537 may be combined with the first hydrogen feed stream 302 of FIG. 3 or with the hydrogen effluent stream 41 of FIG. 1, as disclosed herein.

III.D.2. Effluent Composition

The styrene effluent 51 may comprise $C_8$ arenes wherein an amount of $C_8$ arenes may be at least 60 wt. %; alternatively, at least 70 wt. %; alternatively, at least 75 wt. %; alternatively, at least 80 wt. %; alternatively, at least 85 wt. %; or alternatively, at least 90 wt. %, based upon a total weight of the styrene effluent 51. In a further aspect, an amount of $C_8$ arenes in the styrene effluent 51 may be in range of from about 60 wt. % to about 99.9 wt. %; alternatively, from about 70 wt. % to about 99.8 wt. %; alternatively, from about 75 wt. % to about 99.7 wt. %; or alternatively, from about 80 wt. % to about 99.6 wt. %; or alternatively, from about 85 wt. % to about 99.6 wt. %. In a further aspect, an amount of styrene in the styrene effluent 51 may be at least 85 wt. %; alternatively, at least 87.5 wt. % alternatively, at least 90 wt. %; alternatively, at least 92.5 wt. %; alternatively, at least 95 wt. %; alternatively, at least 97 wt. %; or alternatively, at least 98 wt. %. In a further aspect, the amount of styrene in the styrene effluent 51 may be in a range of from about 85 wt. % to about 99.9 wt. %; alternatively, about 87.5 wt. % to about 99.9 wt. %; alternatively, about 90 wt. % to about 99.9 wt. %; alternatively, about 92.5 wt. % to about 99.9 wt. %; alternatively, about 95 wt. % to about 99.9 wt. %; alternatively, about 97 wt. % to about 99.9 wt. %; or alternatively, about 98 wt. % to about 99.9 wt. %.

IV. Integrated Converting System 1100 with Hydrotreating Process

Figures 6, 7:
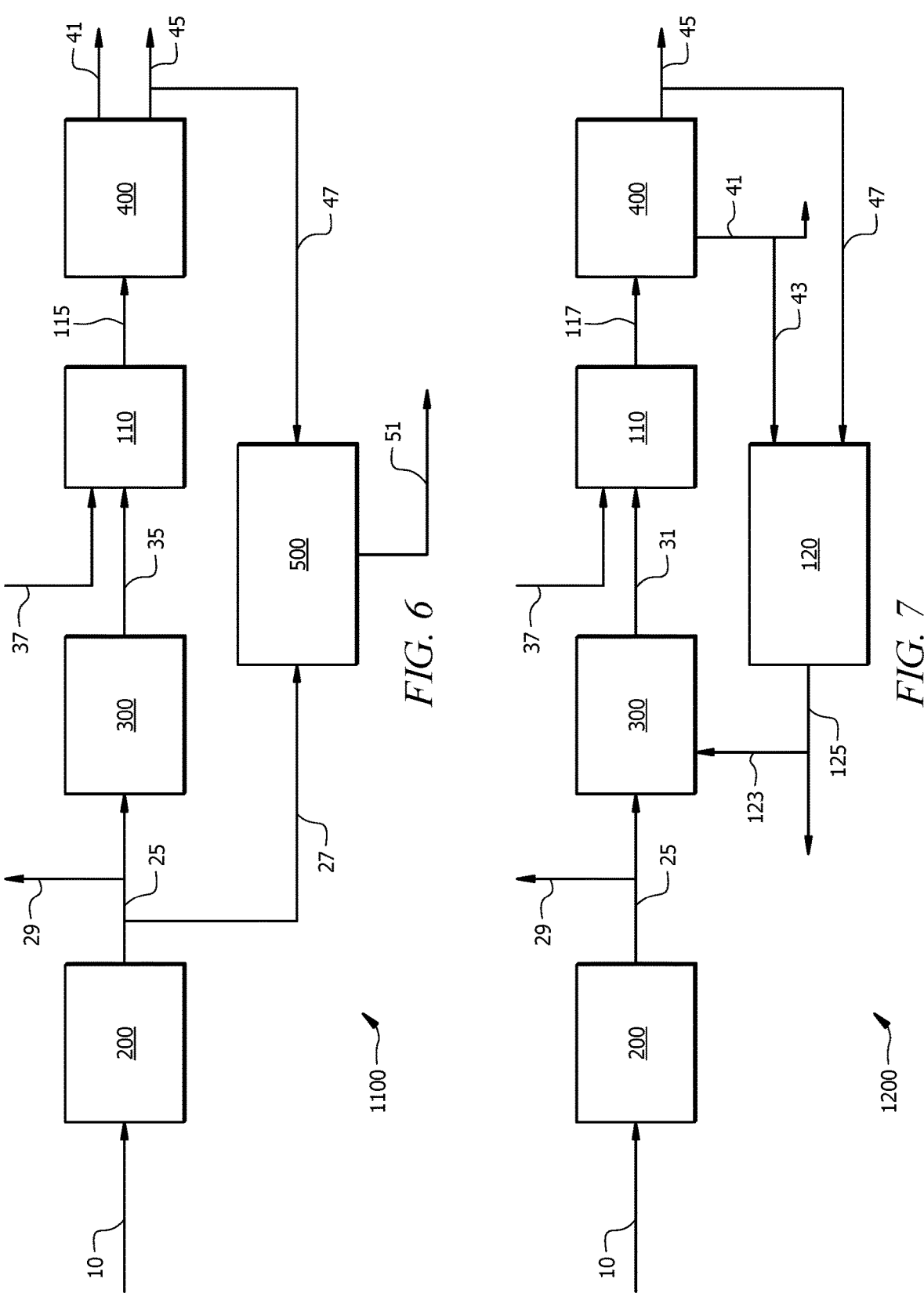
FIG. 6 illustrates a schematic of another integrated converting system.
FIG. 7 illustrates a schematic of another integrated converting system.

Referring to FIG. 6, an integrated converting system 1100 is described wherein like numbers represent like components described in relation to FIG. 1. In contrast to FIG. 1, integrated converting system 1100 comprises hydrotreating process 110 connected between the oligomerization process 300 and the aromatization process 400. In an aspect, hydrotreating process 110 comprises at least one hydrogenation reactor. At least a portion of the 1-hexene comprising the 1-hexene effluent 35 flows into a hydrogenation reactor of hydrotreating process 110 and is contacted with a hydrogenation catalyst to yield a hydrogenation reactor effluent. Within hydrotreating process 110, the hydrogenation reactor effluent passes through a purification stage (not shown), whereby a hexane effluent 115 comprising hexanes (e.g., n-hexanes) is recovered. The hydrogenation catalyst may be contacted with 1-hexenes in any manner suitable for the formation of hexanes. Further processes within hydrotreating process 110 (e.g., fractionation), may impact the amounts of sulfur, nitrogen, and/or aromatic compounds which enter hydrotreating process 110, thereby reducing the amounts of sulfur, nitrogen, and/or aromatic compounds of the hexane effluent 115. In an aspect, hydrotreating process 110 comprises a sulfur removal system. In an aspect, lower amounts of sulfur, nitrogen, and/or aromatic compounds within a feedstock to the aromatization process 400 (e.g., the hexane effluent 115) may result in slower degradation and deactivation of the aromatization catalyst, leading to fewer plant turnarounds and greater aromatics selectivity thereby. In a further aspect, processes within hydrotreating process 110 may enhance the cetane number, the density and/or the smoke point of the components of the hexane effluent 115. In a further aspect, the aromatization auxiliary feed 37 flows into hydrotreating process 110.

In an aspect, the hexane effluent 115 comprises n-hexene. In a further aspect, an amount of n-hexane in the hexane effluent 115 may be at least 85 wt. %; alternatively, at least 87.5 wt. % alternatively, at least 90 wt. %; alternatively, at least 92.5 wt. %; alternatively, at least 95 wt. %; alternatively, at least 97 wt. %; or alternatively, at least 98 wt. %, based upon a total weight of the hexane effluent 115. In yet a further, the amount of n-hexane in the hexane effluent 115 may be in a range of from about 85 wt. % to about 99.9 wt. %; alternatively, about 87.5 wt. % to about 99.9 wt. %; alternatively, about 90 wt. % to about 99.9 wt. %; alternatively, about 92.5 wt. % to about 99.9 wt. %; alternatively, about 95 wt. % to about 99.9 wt. %; alternatively, about 97 wt. % to about 99.9 wt. %; or alternatively, about 98 wt. % to about 99.9 wt. %. In an aspect, an amount of sulfur in the hexane effluent 115 may be in a range of from about 0.01 ppm to about 5 ppm; or alternatively, about 0.05 to about 0.5 ppm. In an aspect, an amount of nitrogen in the hexane effluent 115 may be in a range of from about 0.01 ppm to about 5 ppm; or alternatively, about 0.05 to about 0.5 ppm.

In an aspect, an amount of aromatic components in the hexane effluent 115 may be in a range of from about 0.01 ppm to about 1 ppm; or alternatively, about 0.02 to about 0.2 ppm. The ppm values are weight-weight values based upon the total weight of the hexane effluent 115.

Referring to FIG. 6, the hexane effluent 115 flows into aromatization process 400 in place of the 1-hexene effluent 35. In an aspect, aromatization process 400 of integrated converting system 1100 comprises an aromatization reactor system wherein hexanes (e.g., n-hexane), are contacted with an aromatization catalyst to produce benzene. All other functions and components (e.g., benzene effluent 45), of aromatization process 400 of integrated converting system 1100 operate in a manner similar to aromatization process 400 of integrated converting system 1000 as disclosed herein.

V. Integrated Converting System 1200 with Cyclohexane Production

Referring to FIG. 7, an integrated converting system 1200 is described wherein like numbers represent like components described in relation to FIG. 6. In contrast to FIG. 6, integrated converting system 1200 is absent derivatization process 500 (also can be referred to as an ethylbenzene-styrene production process), as well as the ethylene feed 27 and the styrene effluent 51 associated therewith. Within integrated converting system 1200, a cyclohexane recycle stream 123 flows into oligomerization process 300 wherein cyclohexane functions as a solvent (i.e., diluent). In an aspect, the cyclohexane recycle stream 123 is combined with the solvent feed 308 of FIG. 3 as disclosed herein. The cyclohexane recycle stream 123 comprises a portion of a cyclohexane effluent 125 which flows out of benzene hydrogenation process 120, as further described herein. A mixed $C_6$ effluent 31 flows out of oligomerization process 300 of integrated converting system 1200. In an aspect, the mixed $C_6$ effluent 31 comprises 1-hexene and cyclohexane. The mixed $C_6$ effluent 31 flows into hydrotreating process 110 to produce a mixed hexane effluent 117. In an aspect, the mixed hexane effluent 117 comprises hexanes (e.g., n-hexanes) and cyclohexane. The hexane effluent 117 flows into aromatization process 400 wherein hexanes (e.g., n-hexanes) and cyclohexane are converted in benzene. A portion of the benzene effluent 45 is routed through the benzene feed 47 and a portion of the hydrogen effluent 41 is routed through a reducing feed 43. The benzene feed 47 and the reducing feed 43 flow into benzene hydrogenation process 120 wherein hydrogenation of benzene produces a cyclohexane effluent 125. In an aspect, at least a portion of the cyclohexane effluent 125 comprises cyclohexane and may be routed for storage or for sale. Hydrogenation of benzene may be performed by any means suitable as determined by one having ordinary skill in the art and with the aid of this disclosure. For example, a hydrogenation catalyst can be utilized. Operating conditions within hydrogenation process 120 may be any combination of conditions suitable as determined by one having ordinary skill in the art and with the aid of this disclosure. In an aspect, the temperature and pressure within hydrogenation process 120 may be at levels capable to hydrogenate benzene. In a further aspect, hydrogenation process 120 may have a temperature in a range of from about 10° C. to about 205° C. In yet a further aspect, hydrogenation process 120 may have a pressure in a range of about 360 psig to about 615 psig (about 2.48 MPag to about 4.24 MPag).

In an aspect, an amount of cyclohexane in the cyclohexane effluent 125 may be at least 85 wt. %; alternatively, at least 87.5 wt. % alternatively, at least 90 wt. %; alternatively, at least 92.5 wt. %; alternatively, at least 95 wt. %; alternatively, at least 97 wt. %; or alternatively, at least 98 wt. %, based upon a total weight of the cyclohexane effluent 125. In yet a further aspect, the amount of cyclohexane in the cyclohexane effluent 125 may be in a range of from about 85 wt. % to about 99.9 wt. %; alternatively, about 87.5 wt. % to about 99.9 wt. %; alternatively, about 90 wt. % to about 99.9 wt. %; alternatively, about 92.5 wt. % to about 99.9 wt. %; alternatively, about 95 wt. % to about 99.9 wt. %; alternatively, about 97 wt. % to about 99.9 wt. %; or alternatively, about 98 wt. % to about 99.9 wt. %.

VI. Integrated Converting System 1300 with High Purity 1-Hexene Effluent

Figure 8:
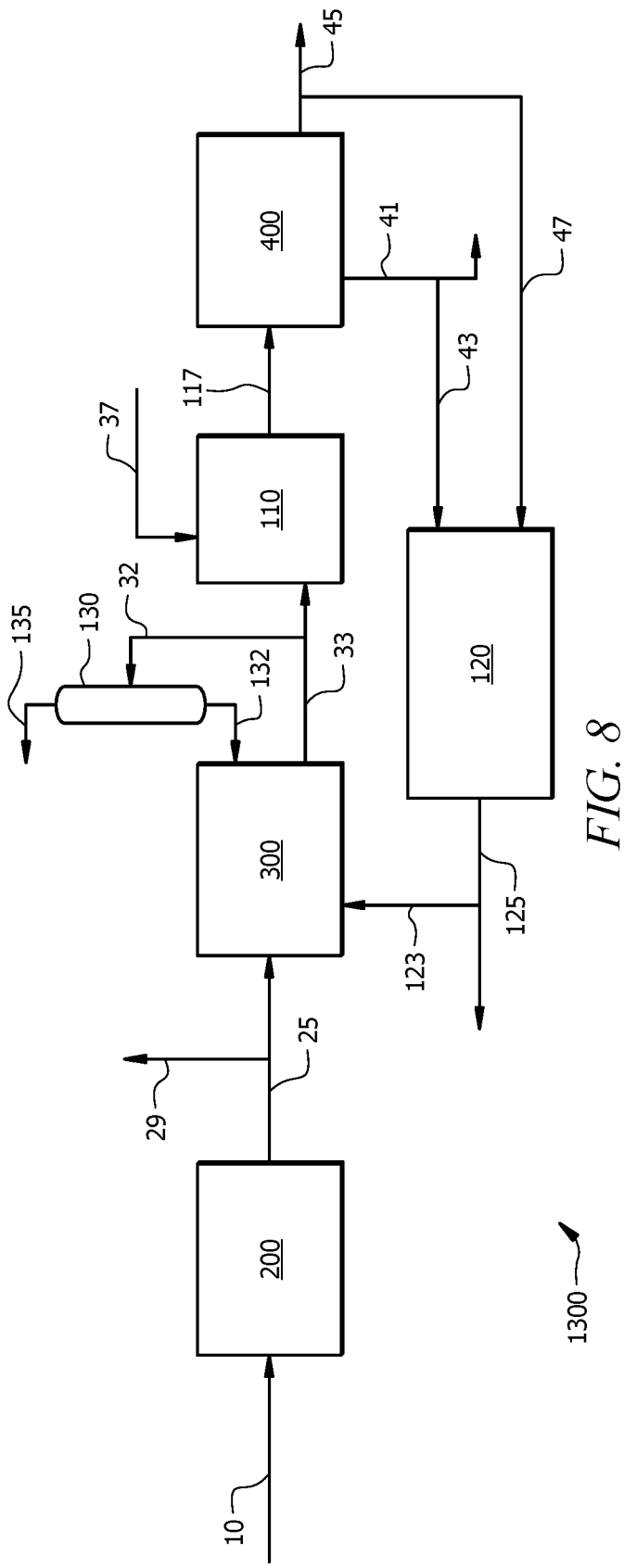
FIG. 8 illustrates a schematic of another integrated converting system.

Referring to FIG. 8, an integrated converting system 1300 is described wherein like numbers represent like components described in relation to FIG. 7. Flowing out of oligomerization process 300 of integrated converting system 1300 is a lower purity 1-hexene (LPH) stream 33. In an aspect, the LPH stream 33 comprises 1-hexene and cyclohexane. A first portion of the LPH stream 33 flows into hydrotreating process 110 to produce the mixed hexane effluent 117 that flows into aromatization process 400. A second portion of the LPH stream 33 is routed through a mixed $C_6$ feed 32 which flows into $C_6$ separator 130. Within $C_6$ separator 130 the mixed $C_6$ feed 32 is separated into a higher purity 1-hexene (HPH) stream 135 and a solvent recycle stream 132. The HPH stream 135 may be routed for storage or for sale. In an aspect, the HPH stream 135 may be used in a polymerization process or in an oligomerization process not associated with an integrated converting system of the present disclosure. In an aspect, the solvent recycle stream 132 may be combined with the cyclohexane recycle stream 123; or alternatively, with the solvent feed 308 of FIG. 3 as described herein. The $C_6$ separator 130 may operate in any manner suitable for producing the HPH stream 135 and the solvent recycle stream 132. In an aspect, $C_6$ separator 130 comprises at least one fractionator.

In an aspect, the HPH stream 135 comprises 1-hexene. In a further aspect, an amount of 1-hexene in the HPH stream 135 may be at least 85 wt. %; alternatively, at least 87.5 wt. % alternatively, at least 90 wt. %; alternatively, at least 92.5 wt. %; alternatively, at least 95 wt. %; alternatively, at least 97 wt. %; alternatively, at least 98 wt. % or alternatively, at least 99 wt. %, based upon a total weight of $C_6$ hydrocarbons in the HPH stream 135. In yet a further, the amount of 1-hexene in the HPH stream 135 may be in a range of from about 85 wt. % to about 99.9 wt. %; alternatively, about 87.5 wt. % to about 99.9 wt. %; alternatively, about 90 wt. % to about 99.9 wt. %; alternatively, about 92.5 wt. % to about 99.9 wt. %; alternatively, about 95 wt. % to about 99.9 wt. %; alternatively, about 97 wt. % to about 99.9 wt. %; or alternatively, about 98 wt. % to about 99.9 wt. %.

VII. Integrated Converting System 1400 with High Purity 1-Hexene Effluent & Ethylene Split Referring to FIG. 9, an integrated converting system 1400 is described wherein like numbers represent like components described in relation to FIG. 8. Prior to flowing into cracking process 200 the hydrocarbon feedstock 10 is combined with an ethane split stream 162, as further disclosed herein. A portion of the cracking process effluent 25 is routed through a utility ethylene stream 29 which flows into $C_2$ separator 160. The utility ethylene stream 29 within $C_2$ separator 160 is separated into an ethylene split stream 165 and the ethane split stream 162. In an aspect, the ethylene split stream 165 may be combined with the ethylene recycle stream 306 of FIG. 3 as disclosed herein. In a further aspect, the ethylene split stream 165 may be used in a polymerization process or in an oligomerization process not associated with an integrated converting system of the present disclosure. In yet a further aspect, the ethylene split stream 165 may be routed for storage or for sale. The $C_2$ separator 160 may operate in any manner suitable for producing the ethylene split stream 165 and the ethane split stream 162. In an aspect, $C_2$ separator 160 comprises at least one fractionator.

In an aspect, the ethylene split stream 165 comprises ethylene. In a further aspect, an amount of ethylene in the ethylene split stream 165 may be at least 85 wt. %; alternatively, at least 87.5 wt. % alternatively, at least 90 wt. %; alternatively, at least 92.5 wt. %; alternatively, at least 95 wt. %; alternatively, at least 97 wt. %; or alternatively, at least 98 wt. %, based upon a total weight of the ethylene split stream 165. In yet a further, the amount of ethylene in the ethylene split stream 165 may be in a range of from about 85 wt. % to about 99.9 wt. %; alternatively, about 87.5 wt. % to about 99.9 wt. %; alternatively, about 90 wt. % to about 99.9 wt. %; alternatively, about 92.5 wt. % to about 99.9 wt. %; alternatively, about 95 wt. % to about 99.9 wt. %; alternatively, about 97 wt. % to about 99.9 wt. %; or alternatively, about 98 wt. % to about 99.9 wt. %.

In an aspect, the ethane split stream 162 comprises ethane. In a further aspect, an amount of ethane in the ethane split stream 162 may be at least 85 wt. %; alternatively, at least 87.5 wt. % alternatively, at least 90 wt. %; alternatively, at least 92.5 wt. %; alternatively, at least 95 wt. %; alternatively, at least 97 wt. %; or alternatively, at least 98 wt. %, based upon a total weight of the ethane split stream 162. In yet a further, the amount of ethane in the ethane split stream 162 may be in a range of from about 85 wt. % to about 99.9 wt. %; alternatively, about 87.5 wt. % to about 99.9 wt. %; alternatively, about 90 wt. % to about 99.9 wt. %; alternatively, about 92.5 wt. % to about 99.9 wt. %; alternatively, about 95 wt. % to about 99.9 wt. %; alternatively, about 97 wt. % to about 99.9 wt. %; or alternatively, about 98 wt. % to about 99.9 wt. %.

VIII. Integrated Converting System 1500 with High Purity 1-Hexene Effluent & Raffinate Referring to FIG. 10, an integrated converting system 1500 is described wherein like numbers represent like components described in relation to FIG. 8. In contrast to FIG. 8, integrated converting system 1500 is absent benzene hydrogenation process 120 as well as the reducing feed 43, the benzene feed 47, the cyclohexane recycle stream 123 and the cyclohexane effluent 125 associated therewith. Flowing into oligomerization process 300 of integrated converting system 1500 is the raffinate stream 419 recovered from purification-extraction process 490 of FIG. 4 as disclosed herein. The raffinate stream 419 is combined with the solvent feed 308 of FIG. 3 wherein one or more components of the raffinate stream 419 may function as a solvent (i.e., diluent) within oligomerization process 300. In an aspect, benzene, toluene, xylene, branched alkanes, or a combination thereof may function as a solvent (i.e., diluent) within oligomerization process 300. The lower purity 1-hexene stream 33 flows out of oligomerization process 300 and integrated converting system 1500 continues as disclosed in relation to FIG. 8.

IX. Integrated Converting System 1600 with Deeper Integration

Figure 11:
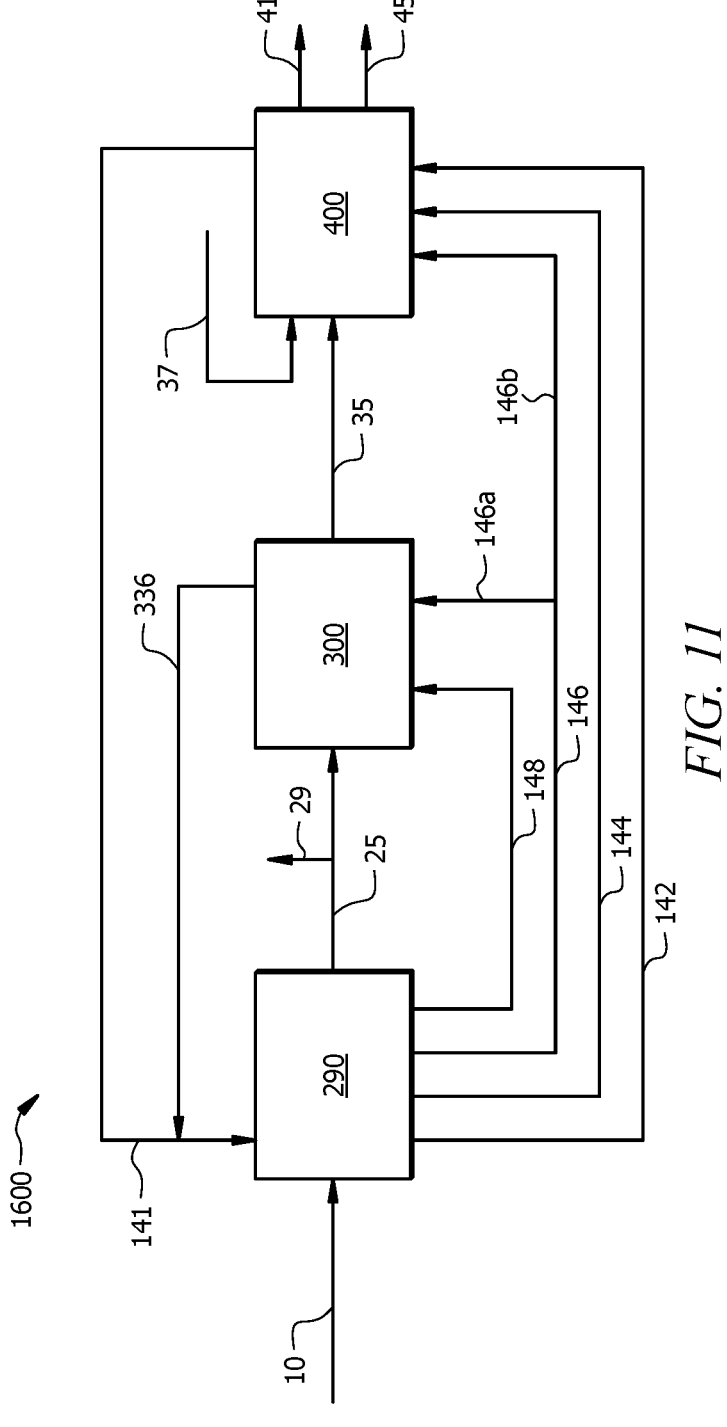
FIG. 11 illustrates a schematic of another integrated converting system.

Referring to FIG. 11, an integrated converting system 1600 is described wherein like numbers represent like components described in relation to FIG. 1. In contrast to FIG. 1, integrated converting system 1600 is absent derivatization process 500 (i.e., ethylbenzene-styrene production process), as well as the ethylene feed 27, the benzene feed 47 and the styrene effluent 51 associated therewith. Within integrated converting system 1600, the hydrocarbon feedstock 10 flows into cracking process 290 which operates in a manner similar to cracking process 200 of FIG. 2, unless otherwise explicitly disclosed. A cracking feed 141 flows into cracking process 290. In an aspect, the cracking feed 141 is combined with the hydrocarbon recycle stream 201 of FIG. 2.

Flowing out of cracking process 290 are the cracking process effluent 25, a light hydrocarbons stream 146, a crude pyrolysis gasoline (CPG) stream 142, a fuel gas stream 144, and a steam effluent 148. The light hydrocarbons stream 146 may be recovered from the cracker effluent 210, the $C_{3+}$ stream 262, and/or the alternate $C_{3+}$ stream 282 of FIG. 2. In an aspect, the light hydrocarbons stream 146 comprises light hydrocarbons produced with cracking process 290 wherein the light hydrocarbons comprise methane, ethane, ethylene, propane, propylene, butane, or combinations thereof. A first portion 146a of the light hydrocarbons stream 146 is routed into oligomerization process 300 and is used for cooling and/or refrigeration therein. A second portion 146b of the light hydrocarbons stream 146 enters aromatization process 400 and is used for cooling and/or refrigeration therein. The steam effluent 148 comprises steam recovered from cracking process 290 (e.g., cracking zone 205), of FIG. 2. The steam effluent 148 flows into oligomerization process 300 and serves as a heat source therein. The CPG stream 142 flows into aromatization process 400 and may be routed to the first reformate stream 417 of FIG. 4. The fuel gas stream 144 enters aromatization process 400. Flowing out of oligomerization process 300 is the heavies effluent 336 of FIG. 3 which, in an aspect, may be combined with the cracking feed 141. Flowing out of aromatization process 400 is the cracking feed 141 which, in an aspect, may be combined with the raffinate stream 419 of FIG. 4.

IX.A. MOGAS Processing

Disclosed herein is a method of enriching a motor fuel stream (i.e., mogas). In an aspect, the mogas comprises the fuel gas stream 144 of integrated converting system 1600. In a further aspect, the mogas is an enriched motor fuel. In a particular aspect, the mogas is enriched by blending therein one or more of the effluent streams generated by an integrated converting system of the present disclosure. For example, the heavies effluent 336, the raffinate stream 419, or a combination thereof may be blended into the mogas.

Described herein is a limited set of operating conditions (e.g., temperature, pressure) for the processes and systems of the present disclosure. One having ordinary skill in the art will appreciate that operating conditions which are not presently disclosed may have any value or, alternatively, range of values, suitable for operation of the processes and systems as disclosed herein. In a further aspect, changes to operating conditions within any of the processes and systems disclosed herein may be implemented by one having ordinary skill in the art with the aid of the present disclosure to maintain operation of the processes and systems disclosed.

X. Advantages

In an aspect, producing benzene with an integrated converting system of the present disclosure can be advantageous in one or more areas when compared to conventional methods of benzene production that utilize non-integrated (i.e., stand-alone) converting processes. Conventional methods of benzene production utilize materials contained in crude oil (e.g., cracking of naphtha) such that the cost of benzene production is linked to crude oil. The present disclosure utilizes ethane contained in natural gas as a starting material (e.g., stream cracking of ethane) such that the cost of benzene production is advantageously decoupled from crude oil. As increasing quantities of natural gas become available, the price of natural gas is decreasing while other factors are increasing demand for benzene. For example, in North America an abundance of ethane for steam cracking has made naphtha cracking uneconomical. There also appears to be the possibility of a potentially significant oversupply of ethylene in the future. A further advantage is that ethylene can be converted into benzene with an integrated converting system of the present disclosure as the market dictates. Also, a further advantage is that ethylbenzene or styrene production can be increased or decreased as the market dictates.

Figure 12:
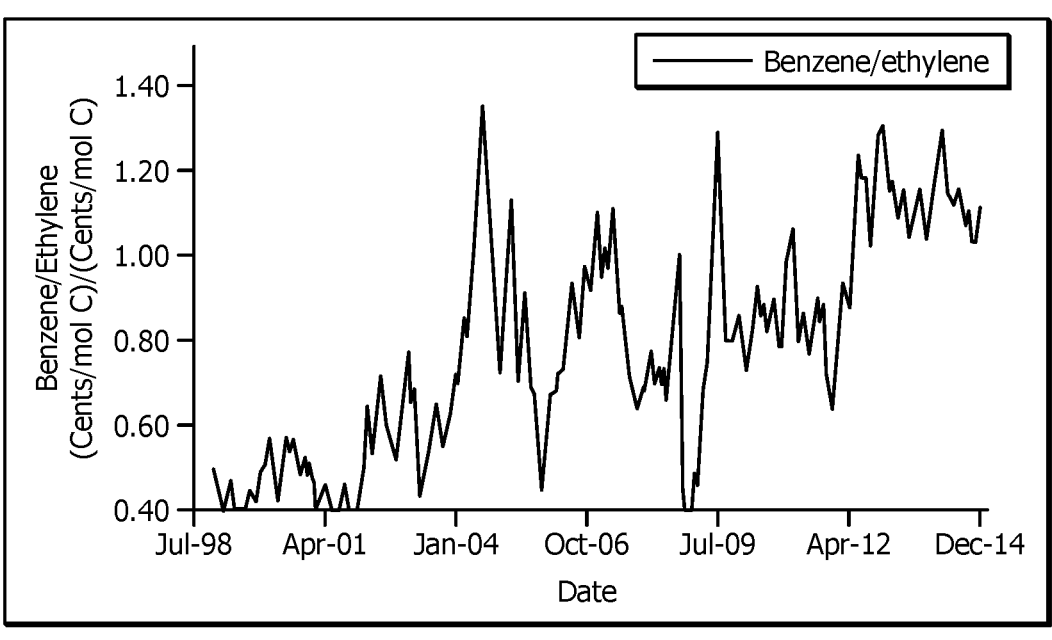
FIG. 12 illustrates a comparison of the price of ethylene with the price of benzene.

FIG. 12 illustrates a comparison of the price of ethylene with the price of benzene on a carbon basis. Data used for creating the graph of FIG. 12 was obtained from IHS Chemical Market Advisory Service. FIG. 12 illustrates how the price of benzene has risen with respect to ethylene over the past 20+ years and would be expected to continually rise in the future. A further advantage of converting ethylene into benzene with an integrated converting system of the present disclosure is the ability to take advantage of the price difference between ethylene and benzene.

A further advantage of an integrated converting system of the present disclosure is the ability to produce large quantities of ethylene, 1-hexene, benzene and styrene and sell portions of each as global demand dictates. An integrated converting system of the present disclosure features flexible modification of the rates of production of the product streams to accommodate changes in demand and/or prices of 1-hexene, benzene, and styrene. In an aspect, as much as 1.5 million tons of ethylene could be produced annually. Other products that can be generated for sale by utilizing an integrated converting system of the present disclosure include hydrogen (i.e., hydrogen effluent 41), styrene (i.e., styrene effluent 51), and cyclohexane (i.e., cyclohexane effluent 125).

A further advantage of an integrated converting system of the present disclosure is that 1-hexene may potentially be used as a feed for the aromatization process. Hydrogenation of 1-hexene to n-hexane as disclosed herein might provide further advantages including slower catalyst deactivation, fewer plant turnarounds, and greater aromatics selectivity. Because the cracking feedstock is derived from natural gas instead of crude oil the 1-hexene/n-hexane being fed to the aromatization process would have a low sulfur content, potentially allowing for the removal of traditional staged combustion air pretreaters and the subsequent lowering of capital cost.

A further advantage of an integrated converting system of the present disclosure is use of light hydrocarbons produced with cracking process 200 in the refrigeration of oligomerization process 300. This approach would allow removal of dedicated refrigeration units within oligomerization process 300 and provide a subsequent lowering of capital cost. A further advantage is that cracking process 200 may produce hydrogen and methane (not shown) which can be used as fuel for heating and/or operating other process within the integrated converting system. This may allow for design improvements to a plant or system such as downsizing heat exchangers.

EXAMPLES

The subject matter having been generally described, the following examples are given as particular aspects of the disclosure and to demonstrate the practice and advantages thereof. It is understood that the examples are given by way of illustration and are not intended to limit the specification of the claims to follow in any manner. It is to be clearly understood that resort can be had to various other aspects, modifications, and equivalents thereof which, after reading the description herein, can be suggest to one of ordinary skill in the art without departing from the spirit of the present disclosure or the scope of the appended claims.

Figure 13:
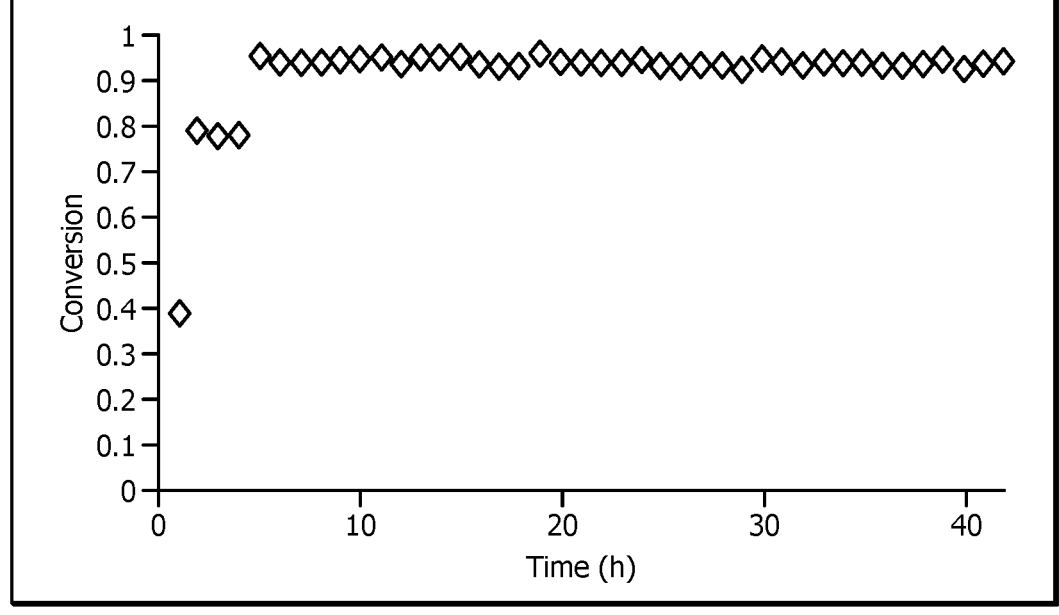
FIG. 13 displays conversion for converting 1-hexene to benzene.
Figure 14:
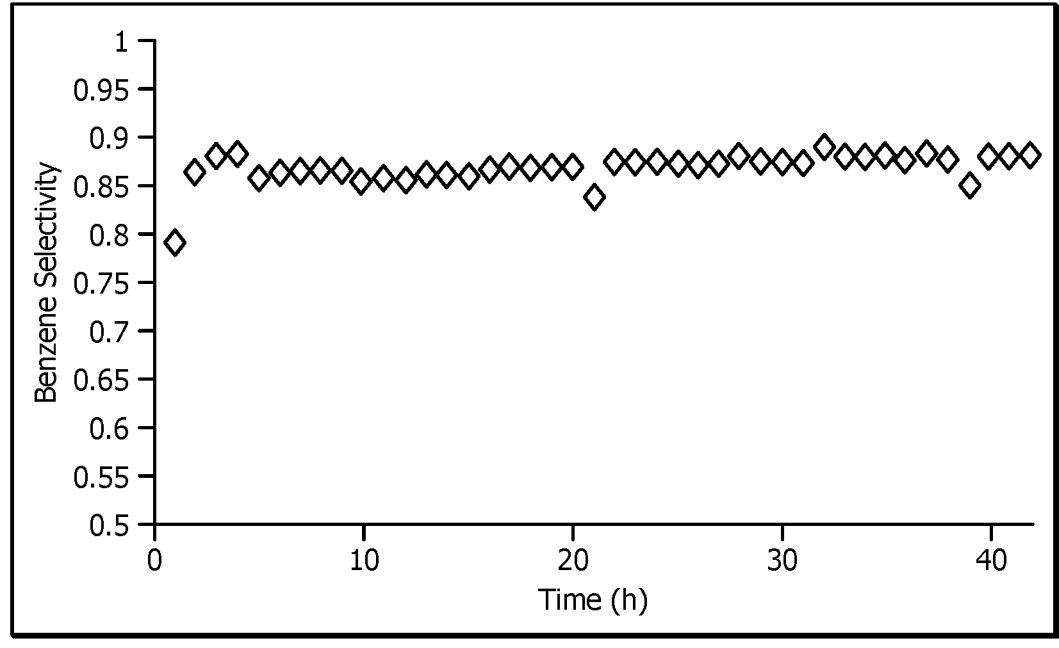
FIG. 14 displays selectivity for converting 1-hexene to benzene.

FIGS. 13 and 14 display results for utilization of an AROMAX® catalyst to produce benzene from 1-hexene. Operating conditions were at a constant temperature of 950° F. (510° C.), a liquid hourly space velocity of 12 h⁻¹, a pressure of 100 psig (0.68 MPag), and a molar ratio of hydrogen to hydrocarbons of 1.2:1. FIG. 13 shows that under the conditions specified conversion for 1-hexene to benzene approaches nearly 100% at around 5 hours. FIG. 14 shows that under the conditions specified, the selectivity for converting 1-hexene to benzene remains at about 85% at around 5 hours. After about 1 hour, the benzene selectivity at the above conditions is approximately 80%.

ADDITIONAL DISCLOSURE

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the detailed description of the present disclosure. The disclosures of all patents, patent applications, and publications cited herein are hereby incorporated by reference.

Aspects of methods and systems have been described. The following are aspects of non-limiting, specific embodiments in accordance with the present disclosure:

In Aspect 1, the techniques described herein relate to a method including: contacting, in an oligomerization reactor, ethylene and an oligomerization catalyst to yield an oligomerization reactor effluent including 1-hexene; recovering 1-hexene from the oligomerization reactor effluent; and contacting, in an aromatization reactor, the 1-hexene recovered from the oligomerization reactor effluent with an aromatization catalyst to yield an aromatization reactor effluent including benzene.

In Aspect 2, the techniques described herein relate to the method of Aspect 1, further including: cracking ethane, propane, butane, pentane, naphtha, or mixtures thereof in a steam cracker to yield a cracker effluent including ethylene; and flowing ethylene recovered from the cracker effluent to the oligomerization reactor.

In Aspect 3, the techniques described herein relate to the method of Aspect 2, further including: recovering light hydrocarbons from the cracker effluent; and using the light hydrocarbons recovered from the cracker effluent for cooling for an oligomerization process containing the oligomerization reactor or for an aromatization process containing the aromatization reactor.

In Aspect 4, the techniques described herein relate to the method of Aspect 2 or 3, further including: recovering steam from the steam cracker; and using the steam recovered from the steam cracker in an oligomerization process containing the oligomerization reactor.

In Aspect 5, the techniques described herein relate to the method any of Aspects 2 to 4, further including: flowing ethylene recovered from the cracker effluent to an alkylation reactor; flowing benzene recovered from the aromatization reactor effluent to the alkylation reactor; and contacting, in the alkylation reactor, the ethylene recovered from the cracker effluent and the benzene recovered from the aromatization reactor effluent with an alkylation catalyst to yield an alkylation reactor effluent including ethylbenzene.

In Aspect 6, the techniques described herein relate to the method of Aspect 5, further including: flowing ethylbenzene recovered from the alkylation reactor effluent to a dehydrogenation reactor; and contacting, in the dehydrogenation reactor, ethylbenzene with a dehydrogenation catalyst to yield a dehydrogenation reactor effluent including styrene.

In Aspect 7, the techniques described herein relate to the method of any of Aspects 1 to 6, further including: flowing at least a portion of 1-hexene recovered from the oligomerization reactor effluent to a hydrogenation reactor; contacting, in the hydrogenation reactor, the at least a portion of 1-hexene with a hydrogenation catalyst to yield a hydrogenation reactor effluent including hexanes; recovering hexanes from the hydrogenation reactor effluent; and contacting, in the aromatization reactor, hexanes recovered from the hydrogenation reactor effluent with the aromatization catalyst to yield the aromatization reactor effluent including benzene.

In Aspect 8, the techniques described herein relate to the method of any of Aspects 1 to 7, wherein the step of contacting ethylene and an oligomerization catalyst is performed in the presence of a diluent selected from the group consisting of isobutane, cyclohexane, methylcyclohexane, n-alkanes, branched alkanes, iso-paraffin solvents, 2,2,4-trimethylpentane, and combinations thereof.

In Aspect 9, the techniques described herein relate to the method of any of Aspects 1 to 8, wherein the 1-hexene is recovered from the oligomerization reactor effluent by washing to remove catalyst and fractionation to remove diluent.

In Aspect 10, the techniques described herein relate to the method of any of Aspects 1 to 9, wherein the oligomerization catalyst includes a chromium source, a pyrrole-containing compound, and a metal alkyl, optionally supported on an inorganic oxide support; and wherein the aromatization catalyst includes a zeolite support, a group VIII metal, and one or more halides.

In Aspect 11, the techniques described herein relate to the method of any of Aspects 1 to 10, wherein a conversion of 1-hexene to benzene is greater than about 70 wt. % based on a total amount of 1-hexene fed to the aromatization reactor.

In Aspect 12, the techniques described herein relate to the method of any of Aspects 1 to 11, wherein a selectivity of 1-hexene to benzene is greater than about 75 wt. % based on a total weight of 1-hexene converted in the aromatization reactor.

In Aspect 13, the techniques described herein relate to the method of any of Aspects 1 to 12, further including: contacting, in a hydrogenation reactor, benzene recovered from the aromatization reactor effluent with a hydrogenation catalyst to yield hydrogenation reactor effluent including cyclohexane; recovering cyclohexane from the hydrogenation reactor effluent; and recycling cyclohexane recovered from the hydrogenation reactor effluent to the oligomerization reactor.

In Aspect 14, the techniques described herein relate to the method of any of Aspects 1 to 13, further including: recovering a lower purity 1-hexene stream from the oligomerization reactor effluent; recovering a higher purity 1-hexene stream from the lower purity 1-hexene stream; and flowing a portion of the lower purity 1-hexene stream to a hydrogenation reactor.

In Aspect 15, the techniques described herein relate to the method of any of Aspects 1 to 14, wherein a sulfur removal system is not used in the step of flowing 1-hexene recovered from the oligomerization reactor effluent to the aromatization reactor.

In Aspect 16, the techniques described herein relate to the method of any of Aspects 1 to 15, wherein the step of contacting ethylene and an oligomerization catalyst is performed in the presence of a diluent recovered from the aromatization reactor effluent, wherein the diluent is selected from a raffinate, benzene, toluene, xylene, branched alkanes, or a combination thereof.

In Aspect 17, the techniques described herein relate to the method of any of Aspects 1 to 16, wherein the oligomerization reactor effluent further includes heavy hydrocarbons having greater than 8 carbon atoms, the method further including: flowing the heavy hydrocarbons recovered from the oligomerization reactor effluent to a steam cracker; and cracking the heavy hydrocarbons in the steam cracker.

In Aspect 18, the techniques described herein relate to the method of any of Aspects 1 to 17, further including: flowing a raffinate recovered from the aromatization reactor effluent to a steam cracker; and cracking the raffinate in the steam cracker.

In Aspect 19, the techniques described herein relate to the method of any of Aspects 1 to 18, wherein the oligomerization reactor effluent further includes a heavy hydrocarbon having greater than 8 carbon atoms, the method further including: blending the heavy hydrocarbon, a raffinate obtained from the aromatization reactor effluent, or both the heavy hydrocarbon and the raffinate into a motor fuel stream.

In Aspect 20, the techniques described herein relate to the method of any of Aspects 1 to 19, further including: flowing hydrogen and light hydrocarbons having less than 6 carbon atoms recovered from the aromatization reactor effluent to a demethanizer, a depropanizer, or both a demethanizer and a depropanizer.

In Aspect 21, the techniques described herein relate to the method of any of Aspects 1 to 20, wherein the ethylene is fed to the oligomerization reactor in a stream including ethylene and ethane.

In Aspect 22, the techniques described herein relate to a system including: an oligomerization reactor configured to contact ethylene with an oligomerization catalyst to yield an oligomerization reactor effluent including 1-hexene; and an aromatization reactor configured to contact 1-hexene recovered from the oligomerization reactor effluent with an aromatization catalyst to yield an aromatization reactor effluent including benzene.

In Aspect 23, the techniques described herein relate to the system of Aspect 22, wherein a conversion of 1-hexene to benzene in the aromatization reactor is greater than about 70 wt. % based on a total weight of 1-hexene fed to the aromatization reactor.

In Aspect 24, the techniques described herein relate to the system of Aspect 22 or 23, wherein a selectivity of 1-hexene to benzene in the aromatization reactor is greater than about 75 wt. % based on a total weight of 1-hexene converted in the aromatization reactor.

In Aspect 25, the techniques described herein relate to the system of any of Aspects 22 to 24, further including: a steam cracker to yield a cracker effluent including ethylene, wherein the oligomerization reactor is configured to receive ethylene recovered from the cracker effluent for oligomerization in the oligomerization reactor.

In Aspect 26, the techniques described herein relate to the system Aspect 25, further including: an alkylation reactor configured to contact benzene recovered from the aromatization reactor effluent and ethylene recovered from the steam cracker with an alkylation catalyst to produce an alkylation reactor effluent including ethylbenzene.

In Aspect 27, the techniques described herein relate to the system of Aspect 26, further including: a dehydrogenation reactor configured to contact ethylbenzene recovered from the alkylation reactor effluent with a dehydrogenation catalyst to produce a dehydrogenation reactor effluent including styrene.

In Aspect 28, the techniques described herein relate to the system of any of Aspects 25 to 27, wherein the cracker effluent further includes light hydrocarbons, wherein an oligomerization process containing the oligomerization reactor, an aromatization process containing the aromatization reactor, or both the oligomerization process and the aromatization process are configured to receive at least a portion of the light hydrocarbons.

In Aspect 29, the techniques described herein relate to the system of any of Aspects 25 to 28, wherein the steam cracker is configured to produce steam, wherein an oligomerization process containing the oligomerization reactor is configured to receive steam recovered from the steam cracker.

In Aspect 30, the techniques described herein relate to the system of any of Aspects 22 to 29, wherein the oligomerization catalyst includes a chromium source, a pyrrole-containing compound, and a metal alkyl, optionally supported on an inorganic oxide support; and wherein the aromatization catalyst includes a zeolite support, a group VIII metal, and one or more halides.

In Aspect 31, the techniques described herein relate to a system that includes: an oligomerization reactor configured to contact ethylene with an oligomerization catalyst to yield an oligomerization reactor effluent including 1-hexene; a hydrogenation reactor configured to contact 1-hexene recovered from the oligomerization reactor effluent with a hydrogenation catalyst to yield an aromatization feed including hexane; and an aromatization reactor configured to contact the aromatization feed with an aromatization catalyst to yield an aromatization reactor effluent including benzene.

In Aspect 32, the techniques described herein relate to the system of Aspect 31, further including: a steam cracker to yield a cracker effluent including ethylene, wherein the oligomerization reactor is configured to receive ethylene recovered from the cracker effluent for oligomerization in the oligomerization reactor.

In Aspect 33, the techniques described herein relate to the system of Aspect 32, further including: an alkylation reactor configured to contact benzene recovered from the aromatization reactor effluent and ethylene recovered from the steam cracker with an alkylation catalyst to produce an alkylation reactor effluent including ethylbenzene.

In Aspect 34, the techniques described herein relate to the system of Aspect 35, further including: a dehydrogenation reactor configured to contact ethylbenzene recovered from the alkylation reactor effluent with a dehydrogenation catalyst to produce a dehydrogenation reactor effluent including styrene.

In Aspect 35, the techniques described herein relate to the system of any of Aspects 31 to 34, wherein the aromatization reactor is further configured to produce a hydrogen effluent, the system further including: a second hydrogenation reactor configured to contact benzene recovered from the aromatization reactor effluent and hydrogen recovered from the hydrogen effluent with a second hydrogenation catalyst to produce a second hydrogenation reactor effluent including cyclohexane, wherein the oligomerization reactor is configured to receive at least a portion of the cyclohexane from the second hydrogenation reactor effluent.

In Aspect 36, the techniques described herein relate to the system of any of Aspects 31 to 35, wherein the oligomerization reactor effluent includes a lower purity 1-hexene stream, the system further including: a C6 separator configured to recover a higher purity 1-hexene stream from a first portion the lower purity 1-hexene stream, wherein the hydrogenation reactor is configured to receive a second portion of the lower purity 1-hexene stream.

In Aspect 37, the techniques described herein relate to the system of any of Aspects 31 to 36, further including: a steam cracker to yield a cracker effluent including ethylene, wherein the oligomerization reactor is configured to receive ethylene recovered from the cracker effluent for oligomerization in the oligomerization reactor; and a C2 separator configured to separate a portion of the cracker effluent into ethylene and ethane, wherein the steam cracker is configured to receive ethane recovered from the C2 separator.

In Aspect 38, the techniques described herein relate to the system of any of Aspects 31 to 37, wherein the oligomerization reactor is configured to receive a raffinate from the aromatization reactor, wherein the raffinate includes benzene, toluene, xylene, branched alkanes, or a combination thereof, wherein the oligomerization reactor effluent includes a lower purity 1-hexene stream, the system further including: a C6 separator configured to recover a higher purity 1-hexene stream from a first portion the lower purity 1-hexene stream, wherein the hydrogenation reactor is configured to receive a second portion of the lower purity 1-hexene stream.

In Aspect 39, the techniques described herein relate to the system of any of Aspects 31 to 38, wherein the oligomerization catalyst includes a chromium source, a pyrrole-containing compound, and a metal alkyl, optionally supported on an inorganic oxide support; and wherein the aromatization catalyst includes a zeolite support, a group VIII metal, and one or more halides.

While several aspects and embodiments of the present disclosure have been shown and described, modifications thereof can be made by one skilled in the art without departing from the spirit and teachings of the present disclosure. The aspects, embodiments, and examples described herein are exemplary only, and are not intended to be limiting. Many variations and modifications of the present disclosure are possible and are within the scope of the subject matter.

Regarding claim transitional terms or phrases, the transitional term "comprising," which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claim. A "consisting essentially of" claim occupies a middle ground between closed claims that are written in a "consisting of" format and fully open claims that are drafted in a "comprising" format. Absent an indication to the contrary, describing a compound or composition as "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a catalyst system consisting of specific components; alternatively, consisting essentially of specific components; or alternatively, comprising the specific components and other non-recited components.

In this disclosure, while systems, processes, and methods are often described in terms of "comprising" various components, devices, or steps, the systems, processes, and methods can also "consist essentially of" or "consist of" the various components, devices, or steps, unless stated otherwise.

The term "about" as used herein means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, alternatively within 5% of the reported numerical value.

Unless indicated otherwise, when a range of any type is disclosed or claimed, for example a range of the number of carbon atoms, molar ratios, temperatures, and the like, it is intended to disclose or claim individually each possible number that such a range could reasonably encompass, including any sub-ranges encompassed therein. For example, when describing a range of the number of carbon atoms, each possible individual integral number and ranges between integral numbers of atoms that the range includes are encompassed therein. Thus, by disclosing a $C_1$ to $C_{10}$ alkyl group or an alkyl group having from 1 to 10 carbon atoms or "up to" 10 carbon atoms, Applicants' intent is to recite that the alkyl group can have 1, 2, 3, 4, 5, 6, 7, 8, 9, or 10 carbon atoms, and these methods of describing such a group are interchangeable. When describing a range of measurements such as molar ratios, every possible number that such a range could reasonably encompass can, for example, refer to values within the range with one significant digit more than is present in the end points of a range. In this example, a molar ratio between 1.03:1 and 1.12:1 includes individually molar ratios of 1.03:1, 1.04:1, 1.05:1, 1.06:1, 1.07:1, 1.08:1, 1.09:1, 1.10:1, 1.11:1, and 1.12:1. Applicants' intent is that these two methods of describing the range are interchangeable. Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. In this aspect, Applicants' disclosure of a $C_1$ to $C_{10}$ alkyl group is intended to literally encompass a $C_1$ to $C_6$ alkyl, a $C_4$ to $C_8$ alkyl, a $C_2$ to $C_7$ alkyl, a combination of a $C_1$ to $C_3$ and a $C_5$ to $C_7$ alkyl, and so forth. When describing a range in which the end points of the range have different numbers of significant digits, for example, a molar ratio from 1:1 to 1.2:1, every possible number that such a range could reasonably encompass can, for example, refer to values within the range with one significant digit more than is present in the end point of a range having the greatest number of significant digits, in this case 1.2:1. In this example, a molar ratio from 1:1 to 1.2:1 includes individually molar ratios of 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, and 1.20, all relative to 1, and any and all sub-ranges and combinations of sub-ranges encompassed therein. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior disclosure.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, $R_l$, and an upper limit, $R_u$, is disclosed, any number falling within the range is specifically disclosed. In particular, the following numbers within the range are specifically disclosed: $R=R_l+k\cdot(R_u-R_l)$, wherein k is a variable ranging from 1 percent to 100 percent with a 1 percent increment, i.e., k is 1 percent, 2 percent, 3 percent, 4 percent, 5 percent, . . . 50 percent, 51 percent, 52 percent . . . 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim.

What is claimed is:

1. A method comprising:
contacting, in an oligomerization reactor, ethylene and an oligomerization catalyst to yield an oligomerization reactor effluent comprising 1-hexene;
flowing at least a portion of 1-hexene recovered from the oligomerization reactor effluent to a hydrogenation reactor;
contacting, in the hydrogenation reactor, the at least a portion of 1-hexene with a hydrogenation catalyst to yield a hydrogenation reactor effluent comprising hexanes;
recovering hexanes from the hydrogenation reactor effluent; and
contacting, in an aromatization reactor, hexanes recovered from the hydrogenation reactor effluent with an aromatization catalyst to yield an aromatization reactor effluent comprising benzene.

2. The method of claim 1, further comprising:
cracking ethane, propane, butane, pentane, naphtha, or mixtures thereof in a steam cracker to yield a cracker effluent comprising ethylene; and
flowing ethylene recovered from the cracker effluent to the oligomerization reactor.

3. The method of claim 2, further comprising:
recovering light hydrocarbons from the cracker effluent; and
using the light hydrocarbons recovered from the cracker effluent for cooling for an oligomerization process containing the oligomerization reactor or for an aromatization process containing the aromatization reactor.

4. The method of claim 2, further comprising:
recovering steam from the steam cracker; and
using the steam recovered from the steam cracker in an oligomerization process containing the oligomerization reactor.

5. The method of claim 2, further comprising:
flowing ethylene recovered from the cracker effluent to an alkylation reactor;
flowing benzene recovered from the aromatization reactor effluent to the alkylation reactor; and
contacting, in the alkylation reactor, the ethylene recovered from the cracker effluent and the benzene recovered from the aromatization reactor effluent with an alkylation catalyst to yield an alkylation reactor effluent comprising ethylbenzene.

6. The method of claim 5, further comprising:
flowing ethylbenzene recovered from the alkylation reactor effluent to a dehydrogenation reactor; and
contacting, in the dehydrogenation reactor, ethylbenzene with a dehydrogenation catalyst to yield a dehydrogenation reactor effluent comprising styrene.

7. The method of claim 1, wherein contacting ethylene and the oligomerization catalyst is performed in a presence of a diluent i) selected from isobutane, cyclohexane, methylcyclohexane, n-alkanes, branched alkanes, iso-paraffin solvents, 2,2,4-trimethylpentane, or combinations thereof, or ii) recovered from the aromatization reactor effluent, wherein the diluent is selected from a raffinate, benzene, toluene, xylene, branched alkanes, or a combination thereof.

8. The method of claim 1, wherein the 1-hexene is recovered from the oligomerization reactor effluent by washing to remove catalyst and fractionation to remove diluent.

9. The method of claim 1, further comprising:
contacting, in the hydrogenation reactor, benzene recovered from the aromatization reactor effluent with the hydrogenation catalyst to yield cyclohexane in the hydrogenation reactor effluent;
recovering the cyclohexane from the hydrogenation reactor effluent; and
recycling the cyclohexane recovered from the hydrogenation reactor effluent to the oligomerization reactor.

10. The method of claim 1, further comprising:
recovering a lower purity 1-hexene stream from the oligomerization reactor effluent;
recovering a higher purity 1-hexene stream from the lower purity 1-hexene stream; and
flowing a portion of the lower purity 1-hexene stream to the hydrogenation reactor.

11. The method of claim 1, wherein a sulfur removal system is not used in flowing 1-hexene recovered from the oligomerization reactor effluent to the aromatization reactor.

12. The method of claim 1, wherein the oligomerization reactor effluent further comprises heavy hydrocarbons having greater than 8 carbon atoms, the method further comprising:
flowing the heavy hydrocarbons recovered from the oligomerization reactor effluent to a steam cracker; and
cracking the heavy hydrocarbons in the steam cracker.

13. The method of claim 1, further comprising:
flowing a raffinate recovered from the aromatization reactor effluent to a steam cracker; and
cracking the raffinate in the steam cracker.

14. The method of claim 1, wherein the oligomerization reactor effluent further comprises a heavy hydrocarbon having greater than 8 carbon atoms, the method further comprising:
blending the heavy hydrocarbon, a raffinate obtained from the aromatization reactor effluent, or both the heavy hydrocarbon and the raffinate into a motor fuel stream.

15. The method of claim 1, further comprising:
flowing hydrogen and light hydrocarbons having less than 6 carbon atoms recovered from the aromatization reactor effluent to a demethanizer, a depropanizer, or both a demethanizer and a depropanizer.

16. A system comprising:

an oligomerization reactor configured to contact ethylene with an oligomerization catalyst to yield an oligomerization reactor effluent comprising 1-hexene;

a hydrogenation reactor configured to contact 1-hexene recovered from the oligomerization reactor effluent with a hydrogenation catalyst to yield an aromatization feed comprising hexane; and an aromatization reactor configured to contact the aromatization feed with an aromatization catalyst to yield an aromatization reactor effluent comprising benzene.

17. The system of claim 16, further comprising:

a steam cracker that cracks ethane, propane, butane, pentane, naphtha, or mixtures thereof to yield a cracker effluent comprising ethylene, wherein the oligomerization reactor receives at least a portion of the ethylene.

18. The system of claim 17, further comprising:

an alkylation reactor that receives at least a portion of the ethylene from the cracker effluent and at least a portion of the benzene from the aromatization reactor effluent, wherein the alkylation reactor is configured to contact the ethylene received from the cracker effluent and the benzene received from the aromatization reactor effluent with an alkylation catalyst to yield an alkylation reactor effluent comprising ethylbenzene.

19. The system of claim 18, further comprising:

a dehydrogenation reactor that receives at least a portion of the ethylbenzene from the alkylation reactor effluent, wherein the dehydrogenation reactor is configured to contact the at least a portion of the ethylbenzene with a dehydrogenation catalyst to yield a dehydrogenation reactor effluent comprising styrene.

* * * * *